(12) United States Patent
Affleck et al.

(10) Patent No.: US 7,596,251 B2
(45) Date of Patent: Sep. 29, 2009

(54) AUTOMATED SAMPLE ANALYSIS SYSTEM AND METHOD

(75) Inventors: Rhett L. Affleck, Poway, CA (US);
Mike Bodnar, San Diego, CA (US);
Robert K. Levin, San Diego, CA (US);
John E. Lillig, Ramona, CA (US);
Robert K. Neeper, Lakeside, CA (US)

(73) Assignee: Nexus Biosystems, Inc., Poway, CA (US)

( * ) Notice: Subject to any disclaimer, the term of this patent is extended or adjusted under 35 U.S.C. 154(b) by 881 days.

(21) Appl. No.: 10/769,462

(22) Filed: Jan. 30, 2004

(65) Prior Publication Data

US 2004/0256963 A1 Dec. 23, 2004

Related U.S. Application Data

(60) Provisional application No. 60/444,519, filed on Jan. 31, 2003, provisional application No. 60/444,585, filed on Jan. 31, 2003, provisional application No. 60/444,586, filed on Jan. 31, 2003, provisional application No. 60/474,989, filed on May 30, 2003.

(51) Int. Cl.
*G06K 9/00* (2006.01)
*A61B 19/02* (2006.01)
*A61C 19/02* (2006.01)
*B01L 9/02* (2006.01)
*A47B 88/06* (2006.01)

(52) U.S. Cl. .................. 382/128; 312/209; 312/294

(58) Field of Classification Search ................ 382/128, 382/153; 312/209, 236, 294, 319.5
See application file for complete search history.

(56) References Cited

U.S. PATENT DOCUMENTS 4,012,665 A * 3/1977 Nakamura et al. ....... 315/241 P (Continued)

FOREIGN PATENT DOCUMENTS

DE 10157121 A1 5/2003

(Continued)

OTHER PUBLICATIONS

Comley, "Compound Management in Pursuit of Sample Integrity", *Drug Discovery World*, 2005, pp. 59-78, Spring 2005.

(Continued)

*Primary Examiner*—John B Strege
(74) *Attorney, Agent, or Firm*—Procopio, Cory, Hargreaves & Savitch, LLP

(57) ABSTRACT

An automated biological sample analysis system and method for use in incubating and analyzing multiple samples for protein crystallization. A temperature controlled cabinet houses sample storage, sample transport, and sample imaging systems. The operation of the system is automated and can be controlled by software, which can be reconfigured remotely. An array of storage shelves includes multiple shelf columns arranged around a core. Multiple banks of removable shelves arranged as magazines are accessed through a door on the cabinet. Each shelf stores a multi-well plate and different sizes can be stored in different shelves. The core houses a sample transport system that includes a multi-axis robot that rotates about a vertical axis to access the shelves in the shelf array. The transport system retrieves and replaces the multi-well plates in the shelves and can move plates from the shelves to an imaging system where each sample can be automatically imaged.

43 Claims, 16 Drawing Sheets

U.S. PATENT DOCUMENTS

| | | | |
|---|---|---|---|
| 4,199,013 A | 4/1980 | Reich et al. | 141/130 |
| 4,422,151 A | 12/1983 | Gilson | 700/283 |
| 4,609,017 A | 9/1986 | Coulter et al. | 141/1 |
| 4,815,845 A * | 3/1989 | Colbaugh et al. | 356/153 |
| 5,105,424 A | 4/1992 | Flaig et al. | 709/243 |
| 5,122,342 A | 6/1992 | McCulloch et al. | 422/65 |
| 5,252,395 A * | 10/1993 | Maruoka et al. | 428/355 AC |
| 5,471,561 A * | 11/1995 | Cowgill et al. | 700/247 |
| 5,539,975 A * | 7/1996 | Kukuljan et al. | 29/701 |
| 5,544,996 A | 8/1996 | Castaldi et al. | 414/280 |
| 5,593,267 A | 1/1997 | McDonald et al. | 414/273 |
| 5,921,739 A | 7/1999 | Keip | 414/273 |
| 6,271,022 B1 * | 8/2001 | Bochner | 435/287.3 |
| 6,360,792 B1 | 3/2002 | Ganz et al. | 141/129 |
| 6,455,861 B1 * | 9/2002 | Hoyt | 250/458.1 |
| 6,545,458 B2 * | 4/2003 | Yamazaki | 324/158.1 |
| 6,637,473 B2 | 10/2003 | Ganz et al. | 141/130 |
| 6,663,334 B2 | 12/2003 | Warhurst et al. | 414/331.14 |
| 6,800,452 B1 * | 10/2004 | McNeil et al. | 435/29 |
| 6,871,922 B1 * | 3/2005 | Pustilnikov | 312/351.14 |
| 6,890,485 B1 * | 5/2005 | Stylli et al. | 422/68.1 |
| 6,977,722 B2 * | 12/2005 | Wohlstadter et al. | 356/246 |
| 6,985,616 B2 | 1/2006 | Ganz et al. | 382/133 |
| 2001/0022913 A1 | 9/2001 | Ohmura | 400/61 |
| 2002/0032762 A1 | 3/2002 | Price et al. | 709/223 |
| 2002/0060464 A1 * | 5/2002 | Bendat et al. | 294/64.1 |
| 2002/0084183 A1 * | 7/2002 | Hanson et al. | 204/224 R |
| 2002/0102149 A1 * | 8/2002 | Warhurst et al. | 414/267 |
| 2002/0155625 A1 * | 10/2002 | Chapman et al. | 436/536 |
| 2003/0138353 A1 * | 7/2003 | Bargoot et al. | 422/58 |
| 2004/0206419 A1 * | 10/2004 | Ganz et al. | 141/130 |

FOREIGN PATENT DOCUMENTS

| | | |
|---|---|---|
| EP | 1348646 A2 | 10/2003 |
| EP | 1614643 A1 | 1/2005 |

OTHER PUBLICATIONS

Johnston, "High-Speed Wide Area, Data Intensive Computing: A Ten Year Retrospective", *7th IEEE Symposium on High Performance Distributed Computing*, May 28, 1998, 1-12, Chicago, Ill.

Krishnan et al., "The XCAT Science Portal", *Proceedings of the 2001 ACM/IEEE conference on Supercomputing (SC2001)*, Nov. 2001, Denver.

Mayo et al., "Benefits of Automated Crystallization Plate Tracking, Imaging, and Analysis", *Structure*, Feb. 2005, pp. 175-182, vol. 13, Elsevier Ltd.

Parvin et al., "Visual Servoing for Online Facilities", *IEEE Computer*, Jul. 1997, pp. 56-62.

* cited by examiner

AUTOMATED SAMPLE ANALYSIS SYSTEM AND METHOD

RELATED APPLICATIONS

This application claims priority to U.S. Provisional Patent Application No. 60/444,519, titled "AUTOMATED SAMPLE ANALYSIS SYSTEM AND METHOD," filed on Jan. 31, 2003, Provisional Patent Application No. 60/444,585, titled "REMOTE CONTROL OF AUTOMATED LABS," filed on Jan. 31, 2003, U.S. Provisional Patent Application No. 60/444,586, titled "AUTOMATED IMAGING SYSTEM AND METHOD," filed on Jan. 31, 2003, and Provisional Patent Application No. 60/474,989, titled "IMAGE ANALYSIS SYSTEM AND METHOD," filed on May 30, 2003, each of which is hereby incorporated by reference for all purposes.

BACKGROUND OF THE INVENTION

1. Field of the Invention

The invention relates to the field of sample analysis. More particularly, the invention relates to an automated biological sample analysis system.

2. Description of the Related Art

Modern chemistry and biology laboratories produce and analyze multiple samples concurrently in order to accelerate the development cycle. The samples are often produced and stored in a sample storage, such as the individual wells in a multi-well plate. A laboratory may simultaneously have tens of thousands of samples prepared for analysis. Automation is needed to provide rapid storage and retrieval of any multi-well plate. However, the amount of laboratory space is limited and it is desirable for an automated system to occupy minimal laboratory space.

However, some types of sample production and analysis must be performed in controlled environments. Often the environment requires refrigeration. For example, in protein crystallography, samples are often incubated for long periods of time at controlled temperatures to induce production of crystals. Hundreds or thousands of samples in sample wells may be periodically viewed or otherwise analyzed to determine the existence of crystals in a sample well.

In a manual process, a technician removes each multi-well plate or sample storage receptacle from a storage location and views each sample well under a microscope. The samples are typically incubated in a refrigerated environment and are highly sensitive to changes in the environment. Thus, typically, the samples are stored in a refrigerated laboratory and the technician removes the sample storage receptacles and views the sample wells under a microscope in the refrigerated room. The need for a refrigerated room expands the amount of laboratory space that needs to be dedicated to protein crystallization and conversely, reduces the amount of laboratory space available for other experiments.

Other problems associated with manually examining each sample well include low throughput and high susceptibility to sample damage due to handling. A technician is unable to process thousands of samples in a short period of time. Additionally, protein crystals are extremely fragile and sensitive to the growth environment. A technician is unable to uniformly handle each sample storage receptacle. The technician transmits different levels of shock and vibration to each of the sample wells when transporting and handling the samples. Even with the utmost of care, the technician can damage the samples due to the amount of shock and vibration imparted by handling the samples.

Some large-scale automated systems minimize the amount of manual handling experienced by a sample. These mega-incubators are designed for extremely large-scale operations. A heavy duty X/Y robot is placed in a temperature controlled room designed to store tens of thousands of sample plates, with each sample plate capable of containing hundreds of samples in individual sample wells. The X/Y robot removes a sample from a storage location and transports it to a single imaging station. The imaging station can be manually operated or can be an automated imaging system that takes an image of the sample.

The mega-incubator systems are designed for large-scale operations and lack the flexibility required in medium sized organizations. For example, the system is housed within a temperature controlled room and requires the entire system be maintained at the same temperature. Multiple samples cannot be tested at multiple temperatures. Additionally, the systems are confined to a single multi-well plate format and hardware in the robot and image system must be reconfigured for changes in the multi-well plate format.

What is needed is a sample imaging system that has the flexibility of manual plate handling and the efficiency of an automated system. The sample imaging system needs to minimize the shock and vibration experienced by the samples. The sample imaging system needs to maintain the samples at a stable environment for long periods of time. Additionally, the laboratory space needed to incubate and analyze the samples needs to be minimized.

SUMMARY OF THE INVENTION

According to one aspect of the invention, an automated biological sample analysis system and method enables incubating and analyzing multiple samples for protein crystallization. A temperature controlled cabinet houses sample storage, sample transport, and sample imaging systems. The system is automated and can be controlled by software, preferably running on a processor external to the cabinet that can be reconfigured remotely. An array of storage shelves includes multiple shelf columns arranged around a core. Multiple banks of removable shelves arranged as magazines are accessed through a door on the cabinet. Each shelf stores a multi-well plate and different sizes can be stored in different shelves. The core houses a sample transport system that includes a multi-axis robot that rotates about a vertical axis to access the shelves in the shelf array. The transport system retrieves and replaces the multi-well plates in the shelves and can move plates from the shelves to an imaging system where each sample can be automatically imaged.

In another aspect of the invention, a transport assembly retrieves storage receptacles from the array of shelves and transports the storage receptacle to a destination. The destination can be another shelf, the imaging system, or an access shelf that is configured to allow removal of the storage receptacle from the cabinet through a plate access door. The transport assembly includes a rotatable platform on which an elevator assembly is mounted. The elevator assembly, in conjunction with the rotatable platform, positions a plate handler at a height and angular position corresponding to a shelf or other location. The plate handler retrieves a storage receptacle from the shelf or other location. The plate handler can also place a storage plate on the shelf or other location.

In another aspect of the invention, a plate handler retrieves or places a storage receptacle, which can be a multi-well plate, from or to a location. The plate handler can retrieve a multi-well plate from a shelf. The plate handler includes fingers that lift a near edge of the multi-well plate above a resting surface while allowing a far edge of the multi-well plate to remain on the resting surface. The plate handler slides the multi-well plate and lifts the far edge of the multi-well plate with a fulcrum. The fulcrum contacts a bottom edge of the well late and lifts the far edge of the multi-well plate as the multi-well plate is slid towards a transport position. To place a multi-well plate the plate handler reverses the retrieval process.

In another aspect of the invention, an imaging system automatically images one or more wells in a multi-well plate or other storage receptacle. An imaging device is connected to a lens and a mount that enables the imaging device and lens to move in a first axis. An imaging station is configured to receive a multi-well plate and can move in a second axis substantially perpendicular to the first axis. The lens is motor driven to allow for automated focusing. The imaging system includes one or more illumination sources. One source can be positioned away from an imaging axis by a first distance. A second illumination source can be positioned away from the imaging axis by a second distance. The first and second illumination sources can be located on substantially opposite sides of the imaging axis. The illumination sources can provide illumination independently. The processor can control the illumination sources to provide illumination simultaneously.

The illumination sources can be xenon flash tubes and the processor can control the duration of the flash. A capacitor or capacitor bank can provide the energy for the flash tubes. A Silicon Controlled Rectifier (SCR) or thyristor can connect the capacitor to the flash tube. The processor can control conduction through the SCR, and thus, energization of the flash tubes. The processor can also interrupt the flow of current through the SCR to control the illumination, or intensity of light.

In another aspect of the invention, a shelf or storage location for the multi-well plates includes locating members for accommodating a plurality of multi-well plate sizes. The shelf is configured to store one multi-well plate from a plurality of multi-well plate sizes. The shelf can be an individual shelf that can be connected to other shelves to produce the shelf array. The shelf includes a first ridge to position a multi-well plate of a first size. The shelf contains a second ridge to position a multi-well plate of a second size. The shelf can position a smaller multi-well plate in a recess defined by the first ridge. The shelf can include a second recess to position a second, larger, multi-well plate. The shelf can contain lateral recesses or gaps in the ridges to locate a multi-well plate and to minimize movement of the multi-well plate along a predetermined direction. The shelf can also include a tab, or flag, extending from a wall of the shelf to interface with a sensor. The flag can interrupt an optical sensor of the transport assembly to allow the transport assembly to locate the plate handler in a position relative to the shelf.

In still another aspect of the invention, a plate tray houses one or more multi-well plates and provides an outline dimension and interface that is analogous to a second multi-well plate. A multi-well plate configuration which is not positioned by the shelf can be installed in the plate tray such that the shelf, plate handler, and transport assembly can manipulate the multi-well plates. The sample analysis system handles the plate tray as if it were the multi-well plate of the same dimension.

In another aspect of the invention a method of imaging one or more wells in a multi-well plate or sample storage receptacle includes retrieving the samples from a shelf using a transport assembly and transporting the multi-well plate to a destination, which can be another shelf, an optical assembly, or an access shelf. The multi-well plate can be transported to an optical assembly and the optical assembly can image at least one of the wells or samples in the multi-well plate. The transport assembly transports the multi-well plate back to a shelf and repositions the multi-well plate on the shelf.

In still another aspect of the invention, a method of transporting a multi-well plate in an imaging system includes raising a first edge of a multi-well plate, transporting or sliding the multi-well plate onto a surface of the plate handler and raising a second edge of the multi-well plate with a fulcrum.

In still another aspect of the invention, a method of imaging at least one well in a multi-well plate includes positioning a multi-well plate along a first axis, positioning an imaging device along a second axis, and capturing an image of at least one well on the multi-well plate.

BRIEF DESCRIPTION OF THE DRAWINGS

The above-described aspects and other aspects, features and advantages of the invention will be apparent upon review of the following detailed description and the accompanying drawings.

DETAILED DESCRIPTION OF THE PREFERRED EMBODIMENT

Figure 1:
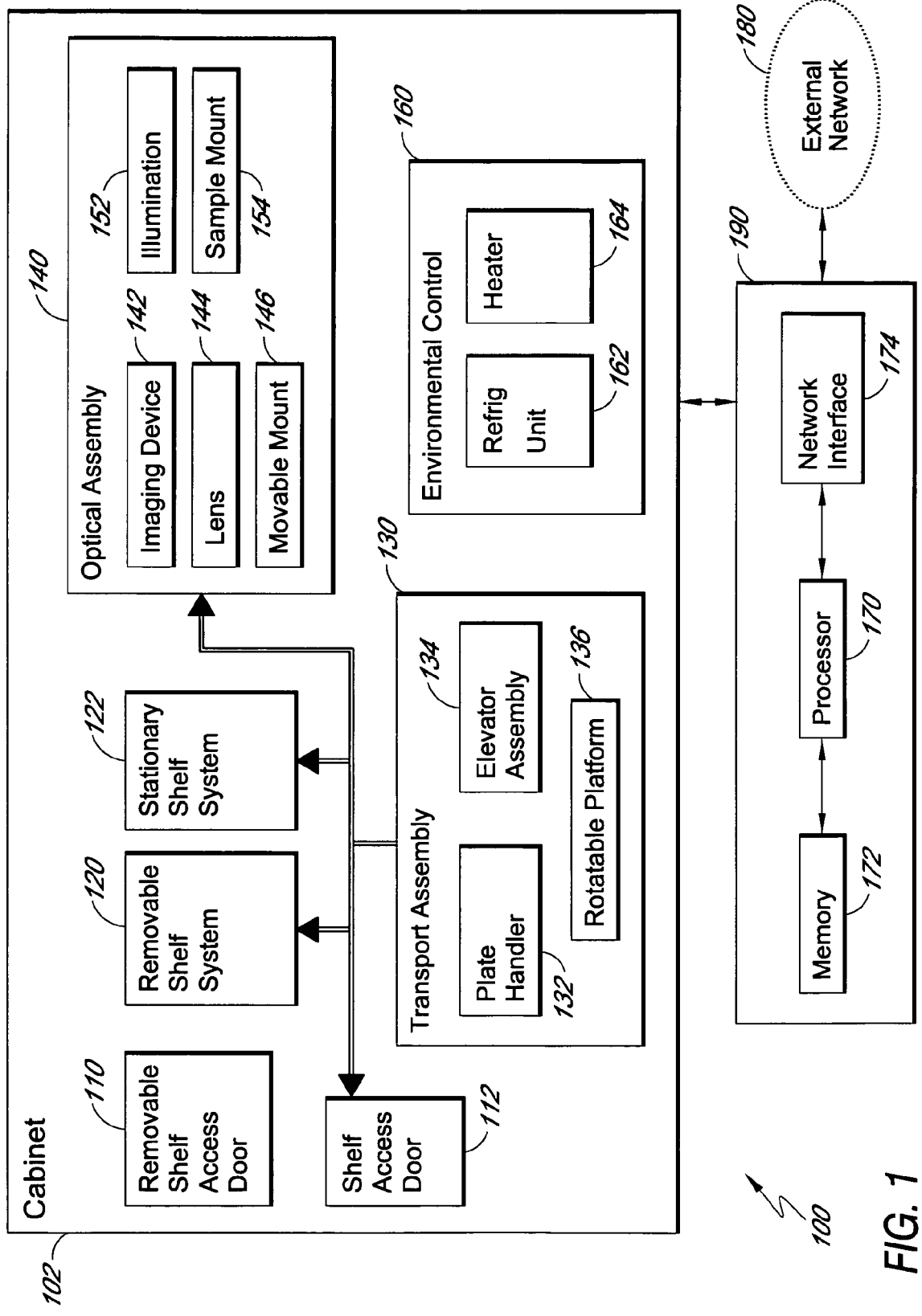
FIG. 1 is a functional block diagram of the automated sample analysis system.

FIG. 1 is a functional block diagram of one embodiment of an automated sample analysis system 100. The automated sample analysis system 100 includes a cabinet 102 including a removable shelf access door 110 and a shelf access door 112 that are typically mounted on a front of the cabinet 102 and provide access to an environmentally controlled chamber within the cabinet 102. The environmentally controlled chamber of the cabinet 102 can also be referred to as the interior of the cabinet 102.

The cabinet 102 also includes spaces that are external to the environmentally controlled chamber. For example, the cabinet 102 includes an environmental control unit 160 mounted external to the environmentally controlled chamber. The environmental control unit includes a refrigeration unit 162 and a heater 164.

The cabinet 102 houses a removable shelf system 120, a stationary shelf system 122, a transport assembly 130 and an optical assembly 140 within the environmentally controlled chamber. The transport assembly 130 includes a plate handler 132, an elevator assembly 134, and a rotatable platform 136. The optical assembly 140 includes an imaging device 142, a lens 144, a movable mount 146, an illumination module 152 and a sample mount 154.

A processor 170 and memory 172 are mounted in a controller 190 that is preferably external to the cabinet 102. The processor 170 is connected to, and in communication with, the memory 172. Additionally, the processor 170 is connected to, and in communication with, a network interface module 174. The network interface module 174 is connected to the cabinet 102 and allows the controller 190 to communicate and control various modules within the cabinet 102. The network interface module 174 can also be connected to an external network 180 that is not a portion of the sample analysis system 100.

The sample analysis system 100 can be used to prepare and analyze numerous types of samples, including biological samples. For example, the sample analysis system 100 can be used to incubate and image protein samples. The sample analysis system 100 can be used to incubate and monitor the protein samples for crystallization. Although the following description details use of the automated sample analysis system 100 in protein crystallization incubation and imaging, the automated sample analysis system 100 is not limited to use in protein crystallization imaging and can be used for other applications.

A user can prepare numerous sample storage receptacles for analysis by the automated sample analysis system 100. The sample storage receptacles can be, for example, tube holders, multi-well plates, microtiter wells, gel plates, flat plates, plates having matrices of drop positions, and the like, or other means for sample storage. For example, a multi-well plate can be one of multiple formats compatible with the shelf systems, 120, 122 within the system 100. The multi-well plate can be, for example, a standard multi-well plate such as a Linbro plate, a Douglas microbatch plate, a Greiner plate, a Corning plate, a 96/384 multi-well plate, or some other type of crystallography plate or sample storage plate. The multi-well plates, or other sample storage receptacles, typically are marked with an identifier. The identifier can be a machine readable identifier, such as a barcode or RF tag. The barcode can include information that correlates with the samples in the multi-well plate or can directly contain information about the multi-well plate or samples. For example, the barcode can include information regarding the type of multi-well plate. This information can then be used, for example, by the transport assembly 130 or the optical assembly 140. For example, the optical assembly 140 can use the multi-well plate identification to determine the number of wells in the multi-well plate and the spacing of the wells.

After the samples are prepared and placed in the multi-well plates, the multi-well plates can be loaded into a removable magazine that includes a number of shelves. The removable magazine can, for example, include sixteen shelves and each shelf can hold one multi-well plate. In another embodiment, the removable magazine includes any number of shelves, such as 10, 12, 14, 18, 20, or 22, for example, and can hold multiple plates, such as in a plate tray (discussed below with respect to FIG. 14), for example. The removable magazine forms part of the removable shelf system 120. The removable shelf system 120 can be configured to accept one or more removable magazines in order to facilitate removal and insertion of multi-well plates. The number of magazines that the removable shelf system 120 can accommodate can be limited in order to minimize the change in environmental conditions experienced in the environmental chamber when the removable shelf access door 110 is opened and one or more magazines are removed. The removable shelf system 120 can include two magazines, with each magazine having sixteen shelves.

The loaded magazine is then inserted into a corresponding location in the removable shelf system 120. The transport assembly 130 then retrieves the plates from a shelf on the magazine and places the multi-well plate on a shelf in the stationary shelf system 122. A barcode reader positioned on the plate handler 132 can read the barcode on the multi-well plate before placing the multi-well plate on a shelf in the stationary shelf system 122. The transport assembly 130 can transmit the barcode to the controller 190 to enable the controller 190 to build a database or allocation table in the memory 172 of the shelf locations and associated multi-well plates contained within the shelves. The controller 190 can control the transport assembly 130 to place multi-well plates retrieved from the removable magazine shelves to stationary shelves. The controller 190 can control the transport assembly 130 to place load the stationary shelves in a predetermined order. Alternatively, the controller 190 can control the transport assembly 130 to search the shelves in the stationary shelf system 122, using a predetermined sequence, for an empty shelf or may simply consult the allocation table stored in memory 172. The transport assembly 1309 can then deliver the multi-well plate to the first empty shelf encountered. In still another alternative, the controller 190 can control the transport assembly 130 to deliver the multi-well plate to a specific empty shelf in the stationary shelf system 122. A typical stationary shelf system 122 includes 300 shelves that can be used for multi-well plate storage. The number of shelves in the stationary shelf system 122 is not limited to 300 but can be any number of shelves. The stationary shelf system 122 is typically an array of shelves that are arranged in an arc or otherwise arranged around a core.

As described further below, plates of various sizes may be used in the sample analysis system. In one embodiment, the dimensions of the shelves are large enough to hold all sizes of plates. In another embodiment, some shelves are dimensioned to hold smaller plates and other shelves may be dimensioned to hold larger plates. In this embodiment, the smaller plates may be stored in smaller shelves, thus reducing the amount of storage space that is unused when small plates are stored on shelves dimensioned to hold larger plates.

Once the transport assembly 130 has placed all of the multi-well plates from the magazines to locations in the stationary shelf system 122, the magazine can be removed to be reloaded with additional multi-well plates. The process can be repeated until all of the shelves in the stationary shelf system 122 contain a multi-well plate. Alternatively, some shelves in the stationary shelf system 122 can remain empty. Typically, the system 100 operates with the removable magazines empty to allow multiple multi-well plates to be retrieved from locations and placed into the magazines for removal from the system 100. Alternatively, the system 100 can operate with the removable magazines loaded with multi-well plates to increase the total multi-well plate capacity of the system 100.

As noted above, the controller 190 controls the transport assembly 130 to retrieve and transport multi-well plates from the removable magazines to the stationary shelves. The transport assembly 130 can move multi-well plates in any order. The transport assembly 130 has random access to the shelves. Additionally, the transport assembly 130 can perform the complementary task of removing multi-well plates from shelves in the stationary shelf assembly 122 and transporting and delivering the multi-well plates to shelves in the removable magazines. The transport assembly 130 performs nearly all of the multi-well plate transportation within the system 100. The transport assembly 130 can retrieve multi-well plates from, and transport multi-well plates to, a variety of locations. For example, the transport assembly 130 can transport a multi-well plate to a shelf that is accessible via the shelf access door 112. The shelf access door 112 provides user access to a single shelf to allow removal or insertion of a single multi-well plate. The shelf access door 112 provides an alternative to using the removable magazines to remove a multi-well plate. The shelf access door 112 is typically much smaller than the removable shelf access door 110 and thus, minimizes the effects on the environmental chamber when opened.

The transport assembly 130 can also transport multi-well plates to, and retrieve multi-well plates from, an optical assembly 140. Typically, the transport assembly moves plates between the optical assembly 140 and the stationary shelf system 122. However, the processor can control the transport assembly 130 to move plates between any originating locations to any destination.

The transport assembly 130 includes at least one plate handler 132, an elevator assembly 134, and a rotatable platform 136. The transport assembly 130 is located within the controlled environment chamber of the cabinet 102 and is also located inside the arc defined by the stationary shelf system 122. Alternatively, where the stationary shelf system is arranged around a core, the transport assembly 130 is located within the core.

The transport assembly 130 includes a plate handler 132 that is configured to move a plate into and out of a shelf. The plate handler 132 is mounted to the elevator assembly 134. The elevator assembly 134 moves the plate handler up and down to the various heights corresponding to the heights of the shelves in the stationary shelf system 122. The elevator assembly 134 is mounted on the rotatable platform 136. The rotatable platform 136 can rotate about a vertical axis and can position the elevator assembly 134 and plate handler 132 at an angular position corresponding to a column of shelves in the stationary shelf system 122. Thus, the transport assembly 130 is a four axis robot that can position a multi-well plate in X, Y, and Z axis and can rotate about a vertical axis extending through the rotatable platform 136.

In one embodiment, multi plate sizes may be stored on the shelves and transported by the plate handler 132 to the optical assembly 140. In one embodiment, the optical assembly 140 includes a mount configured to support a plate of a standard size. The optical assembly 140 may also include a moveable plate adapter having a footprint the size of a standard plate that is configured to support plates that are smaller than the standard size. Accordingly, when a plate that is smaller than the standard size is to be placed in on the mount of the optical assembly 140, the plate adapter may first be placed on the mount, by the plate handler 132, for example, and then the smaller plate may be placed on the plate adapter. In this way, the optical assembly 140 is able to easily acquire images from various sizes of plates through the use of the plate adapter. In one embodiment, the optical assembly 140 includes multiple plate adapters, each having a footprint the size of a standard plate and each being configured to support a plate of a different, smaller size. In this embodiment, the plate handler 132 may select a plate adapter based on the size of the plate which is to be placed on the mount of the optical assembly 140.

The optical assembly 140 includes an imaging device 142, a lens 144, a movable mount 146, an illumination module 152, and a sample mount 154. The optical assembly 140 is located within the environmentally controlled chamber of the cabinet 102. The optical assembly 140 receives a multi-well plate from the transport assembly 130 at the sample mount 154. The sample is moved in a first axis using the sample mount 154. The movable mount 146 positions the imaging device 142 and lens 144 over at least one well of the multi-well plate. The illumination module 152 lights the sample and the imaging device 142 captures the image of the sample.

The sample mount 154 is configured to position the multi-well plate in a predetermined axis. The sample mount 154 can also include a filter mount that is configured to hold optical filters. For example, the filter mount can hold polarization plates or light filtering plates. Typically, the sample mount 154 is configured to move along a linear axis. However, the sample mount 154 can be configured to position the multi-well plate by moving on more than one axis.

The lens 144 is connected to the imaging device 142. The imaging device 142 can be a camera or other image capture device. For example, the imaging device 142 can be a film camera, a digital camera, a CMOS camera, a Charge Coupled Device (CCD), and the like, or some other means for imaging. For example the imaging device 142 can be a CMOS camera with a firewire interface. The CMOS camera communicates with the controller 190 through the network interface 174 using a firewire connection. Such a CMOS camera is capable of providing five images per second to the controller 190. However, other practical limitations, such as the time required between successive illuminations in the illumination module 152 can reduce the throughput of the optical assembly 140. Capacitors driving flash tubes in the illumination module 152 can require nearly one second to recharge. Additional constraints include the desire to minimize the acceleration and speed imposed on the multi-well plate, as well as auto focusing of the lens 144 and imaging device 142 prior to each image capture. Taking into account X/Y positioning of the samples in the multi-well plate, auto-focusing, imaging of each sample in the multi-well plate, and charging time of the illumination module 152, the optical assembly 140 can average approximately one image in five seconds. However, the image throughput increases if the optical assembly 140 takes more than one image per sample. Other factors can also affect the image throughput. For example, the controller 190 can implement an automatic sample location routine rather than using a predetermined map of sample positions. Additionally, the controller 170 can instruct the lens 144 and imaging device 142 to capture a zoomed image. Thus, taking into account the various factors, the optical assembly 140 can capture and transmit to the controller 190 on average one image in five seconds. Alternatively, the optical assembly 140 can capture and transmit one image in as little as 0.2 seconds or as great as 12 seconds, and the time to capture and transmit an image can be 1, 2, 3, 4, 5, 6, 7, 8, 9, 10, 11, or 12 seconds. The optical assembly 140 can capture and transmit one image, on average, in 5-12 seconds.

The imaging device 142 is not limited to capturing a visible image but can be configured to capture some other characteristic, such as radiation spectra, x-ray images, infrared images, ultraviolet images, spectrally filtered images, and the like. The controller 190 can control a motorized zoom and motorized focus included on the lens 144. In one embodiment, the controller also controls a motorized aperture. In another embodiment, the imaging device includes a motorized filter wheel that may be rotated, either automatically or manually, in order to change a filter through which images are acquired. For example, the motorized filter wheel may include a polarization filter. The lens 144 can advantageously have a zoom function, such as a 12-1 zoom and, in cooperation with the imaging device 142, can easily provide 3-4 micron optical resolution. Alternatively, the lens 142 and imaging device 142 can be integrated as a single assembly, such as a camera or microscope having a lens. When used with a high-intensity light source, as described below, the imaging device 142 in combination with the lens 144 provides a broad depth of field to allow imaging of objects such as protein crystals at varying depths within the sample well.

The imaging device 142 and lens 144 are mounted on the movable mount 146. The movable mount 146 can move in a predetermined axis and can position the imaging device 142 and lens 144 at a location along the axis. The movable mount 146 typically moves along a linear axis that is substantially perpendicular to the moving axis of the sample mount 154. Typically, the movable mount 146 and sample mount 154 move across a plane that is substantially parallel to a plane defined by the multi-well plate located in the sample mount 154. Thus, the controller 190 can control the movable mount 146 and the sample mount 154 to position a specific well in the multi-well plate to be within the view of the lens 144 and imaging device 142.

The optical assembly 140 also includes an illumination module 152 that illuminates the sample for imaging by the imaging device 142. The samples that are to be imaged are often highly sensitive to temperature changes. The illumination module 140 is configured to minimize the amount of heat transferred to the sample when the sample is illuminated. The system can use incandescent or fluorescent light sources illuminating an optical light pipe, such as an optical fiber. The optical fiber can then be routed to the sample such that the sample is illuminated by light travelling through the light pipe. The light sources can remain illuminated during the entire multi-well plate imaging process. However, such an illumination system can still generate too much heat exposure to the samples and can result in unsatisfactorily low levels of light. LED sources can be used to illuminate the sample, but LED radiation occupies a narrow optical bandwidth and is typically low intensity. LEDs can emit nearly a single wavelength and can require expensive imaging systems to compensate for the lack of light.

In one preferred embodiment, the illumination module 152 can include one or more flash tubes to momentarily illuminate the sample with relatively high-intensity light during the period in which the imaging device 142 captures an image of the sample. The flash tubes can be xenon flash tubes that provide a broad spectrum of light. The flash tubes are on only for a small fraction of a second per image and transfer almost no heat to the samples. Multiple tubes can be positioned to provide both on-axis and off-axis lighting of the sample. For example, a first xenon tube can be positioned a first distance from the imaging axis of the imaging device 142. A second xenon tube can be positioned a second distance from the imaging axis of the imaging device 142. In one embodiment, the first and second distances are equal and the first xenon tube is positioned opposite the imaging axis from the second xenon tube.

When two xenon tubes are positioned off the imaging axis, the processor can control the flash tubes to provide on-axis or off-axis illumination of the sample. One xenon tube can illuminate the sample to provide off-axis illumination. Both xenon tubes can illuminate simultaneously to provide on-axis illumination. A fan is advantageously provided to direct heat produced by the tubes outside of the cabinet 102.

Off-axis lighting tends to create subtle shadows on small objects in the target area viewed by the image device 142. The shadows caused by off-axis lighting make the objects much more visible than simple direct lighting of the sample from below. The controller 190 can control the imaging device 142 to capture two images of the sample. The imaging device 142 captures one image with the illumination module 152 lighting the sample with the first xenon flash tube. The imaging device 142 captures a second image with the illumination module 152 lighting the sample with the second xenon flash tube. The controller 190 can then combine the image data and perform an analysis based on the combined data. The processor 170 can perform an accurate analysis of small objects in the sample using the combined data. The processor 170 can, for example, use processor readable instructions stored in memory 172 to perform image analysis on a single image, multiple, or combined images. Alternatively, a user or operator can view the captured images.

The sample analysis system 100 also includes an environmental control unit 160 that is located within the cabinet 102 but not within the environmentally controlled chamber of the cabinet 102. Thus, the environmental control unit 160 is mounted on the exterior of the cabinet 102. A face plate or cover (not shown) can be used to shield the environmental control unit 160 to give the cabinet 102 a more pleasing appearance.

The environmental control unit 160 is typically configured to control a temperature within the environmentally controlled chamber, or interior, of the cabinet 102. The environmental control unit 160 can, for example, maintain the temperature within the interior of the cabinet 102 at any temperature within the range of 4° to 40° C. The environmental control unit 160 can preferably maintain the temperature to an accuracy of +/−1° C. or better. The environmental control unit 160 can also be configured to control other aspects of the interior of the cabinet 102. For example, the environmental control unit 160 can be configured to control an atmosphere, humidity, pressure, and the like within the interior of the cabinet 102. The atmosphere can be a dry nitrogen atmosphere for example.

One embodiment of the environmental control unit 160 includes a refrigeration unit 162 and a heater 164 to control the temperature within the interior of the cabinet 102. Because the environmental control unit 160 typically includes mechanical equipment such as fans, compressors, and pumps within the sub assemblies, the amount of vibration generated by the environmental control unit can be substantial. The environmental control unit 160 is preferably mechanically isolated from the interior of the cabinet 102 to minimize the vibration transferred to the samples. One way to accomplish this is to have the environmental control unit 160 separately supported by the support surface that supports the cabinet 102. Thus, in operation, the environmental control unit 160 is not mounted to the cabinet 160 but instead, rests on a support surface. The support surface can be, for example the ground, laboratory floor, or other means for supporting the cabinet 102. Alternatively, the support surface can be isolated from the cabinet 102 support surface. For example, the cabinet 102 can be mounted to the floor and the environmental control unit 160 can rest on a vibration dampened floor that is isolated from the laboratory floor. The environmental control unit 160 is thus coupled to the cabinet 102 using the minimal number of connections required to transfer the heating or cooling air to the interior of the cabinet 102.

Control elements of the sample analysis system 100 are mounted outside of the cabinet 102 and are typically mounted remote from the cabinet 102. The cabinet 102 can include a port that provides a connection to all the controllable assemblies contained by the cabinet 102. For example, the transport assembly 130, optical assembly 140, and environmental control unit 160 can all be controlled through a common communication bus. Alternatively, each controlled device can be controlled using independent control lines, or independent control channels. In another alternative, some of the controlled devices can be controlled through a common bus and others can be controlled using dedicated control lines or control channels. Similarly, the controller 190 can communicate with the various devices and assemblies using a common bus, dedicated lines, or channels.

The controller 190 communicates with the various devices associated with the cabinet 102 via a network interface 174. The network interface 174 translates the processor 170 commands to the communication protocol used by the destination device. Conversely, the network interface 174 translates received communication messages to processor 170 readable data or messages. The network interface 174 can also interface the processor 170 to an external network 180 that is not part of the sample analysis system 100. The external network 180 can be, for example, a local area network or a wide area network, such as the Internet.

The processor 170 is also connected to the memory 172 that can include volatile memory and non-volatile memory. The memory 172 can be a combination of integrated circuits, optical memory, and magnetic memory. The memory 172 can store processor readable instructions, such as embedded code, that instruct the processor 170 to control the assemblies and devices of the cabinet 102. The processor readable instructions can be configurable or can be a fixed configuration. For example, the processor readable instructions can be configured via a user interface to direct the processor 170 to instruct the transport assembly 130 to retrieve a specific multi-well plate and deliver it to the optical assembly 140. The optical assembly 140 can then be controlled to image a particular well in the multi-well plate. The controller 190 also stores captured images in memory 172. The captured images can then be viewed on a display (not shown) or transmitted to a remote location for further analysis or display. The memory 172 can include storage such as hard disk storage or RAID storage to store the captured images. The memory 172 can include, for example, 500 GB of memory for image storage.

The controller 190 is typically housed within a computer, controller, or server. The controller 190 can be located remote from the cabinet 102 and is typically not mounted to the cabinet 102 in order to minimize coupling of vibrations and heat generated by the controller 190 to the environmentally controlled chamber of the cabinet 102.

Figure 2:
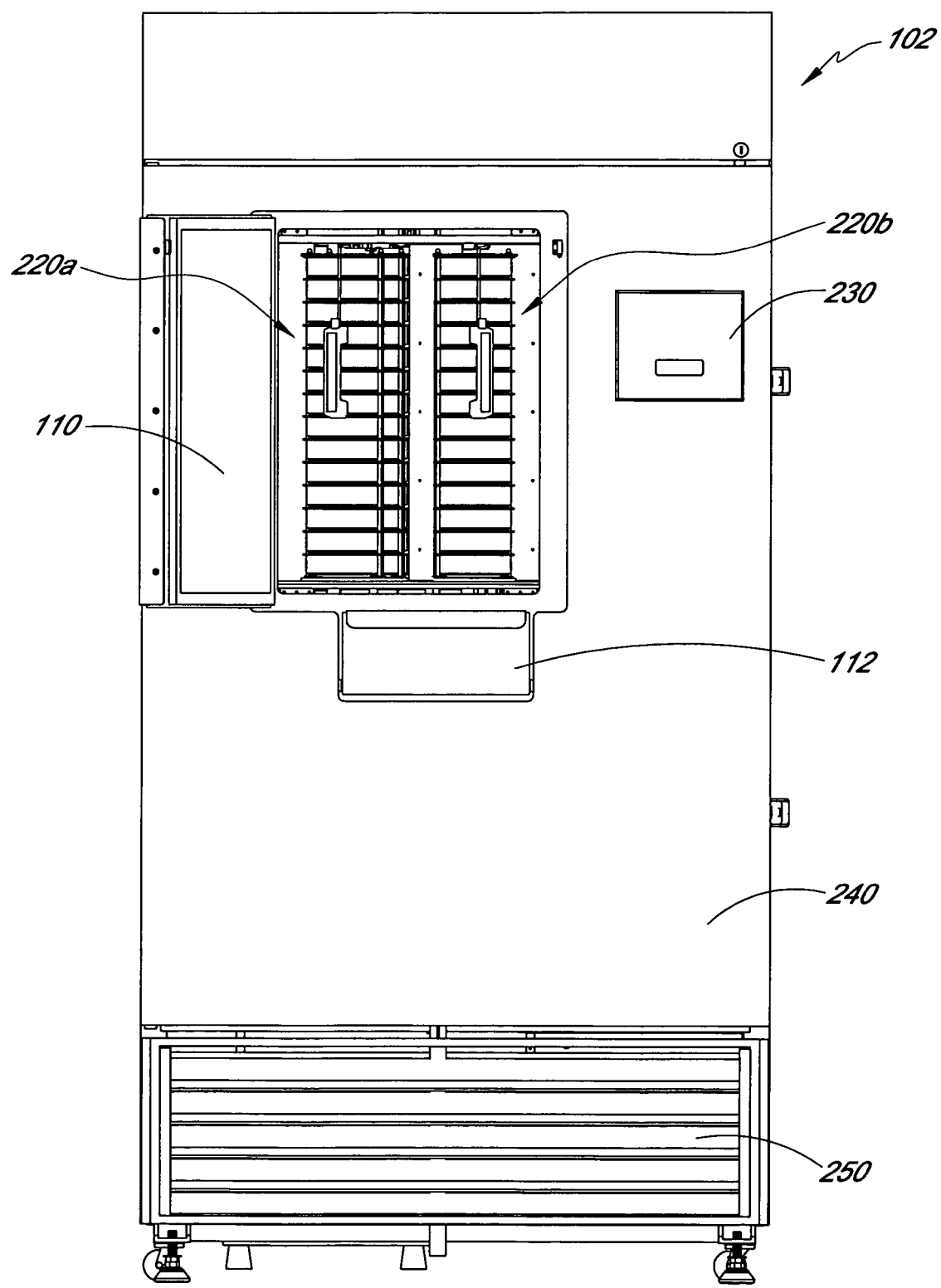
FIG. 2 is a partial view of the cabinet front.

FIG. 2 is a view of the front of the cabinet 102 that was detailed in FIG. 1. The front of the cabinet 102 includes the removable shelf access door 110 and the shelf access door 112. The removable shelf access door 110 is shown in its open position. Two removable magazines 220a and 220b are accessible through the removable shelf access door 110. The two removable magazines 220a and 220b form part of the removable shelf system 120 discussed in conjunction with FIG. 1. The cabinet 102 is not limited to housing two removable magazines 220a and 220b. Also, the location of the removable shelf access door 110 is not limited to the front of the cabinet 102. However, because the removable shelf access door 110 provides access to the environmentally controlled interior of the cabinet 102, the size of the removable shelf access door 110 is directly related to the change in environmental conditions caused by opening the door. The size and number of removable magazines 220a and 220b can then be determined based on the size of the removable shelf access door 110.

The front of the cabinet 102 also preferably includes the shelf access door 112 that provides access to one multi-well plate. A single multi-well plate can be loaded into the cabinet 102 via the shelf access door 112. Additionally, the processor can control the transport assembly to deliver a single multi-well plate to the shelf access door for removal from the cabinet 102. The shelf access door 112 is typically smaller than the removable shelf access door 110 to further minimize changes to the interior environment when the door is opened. The placement of the shelf access door 112 is typically at a height and position that is convenient for user access. However, the placement of the shelf access door 112 is not limited to any particular location and is not limited to placement on the front of the cabinet 102.

The front of the cabinet 102 also includes a front door 240 that provides access for installation and maintenance. The operation of the sample analysis system typically does not require accessing the front door 240. The front door 240 can include an environmental monitor 230 that indicates, for example, the temperature of the interior of the cabinet 102. The environmental monitor 230 can also provide local controls to allow a user to modify the interior environment. For example, the environmental monitor 230 can provide controls to change the temperature within the interior of the cabinet 102. Below the front door 240 is a front access panel 250 that provides access to the portion of the environmental control unit (not shown) that is housed in the lower portion of the cabinet 102 outside of the environmentally controlled interior of the cabinet 102.

Figure 3:
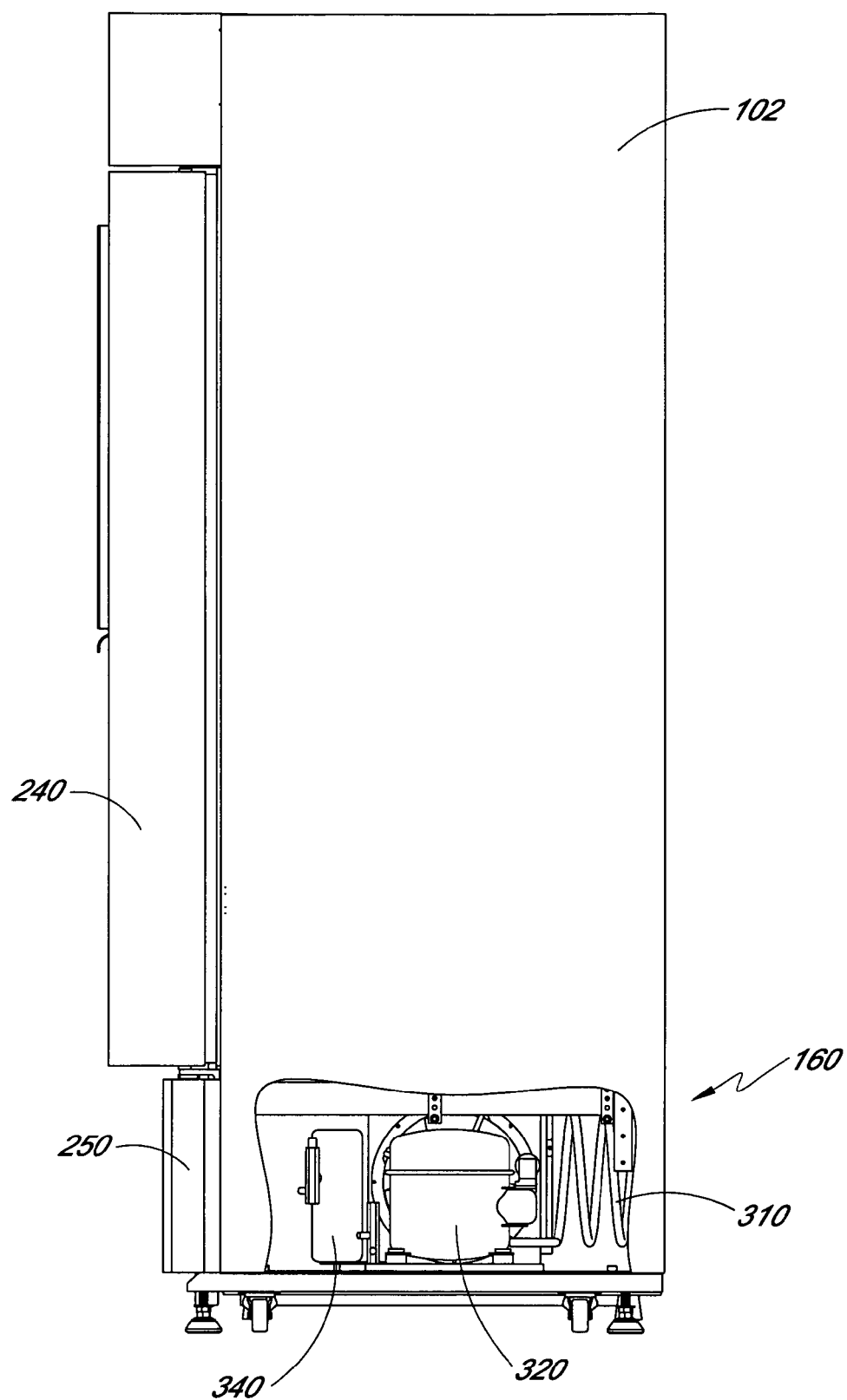
FIG. 3 is a partial view of the cabinet side.

FIG. 3 is a side view of the cabinet 102 having a cut away view showing the placement of the environmental control unit 160 in a lower portion of the cabinet 102 behind the front access panel 250. The environmental control unit 160 can include a refrigerant pump or compressor 320 and condenser 340. A motorized fan 330 can cool the condenser 340. Refrigerant lines 310 can carry the refrigerant to, for example, an evaporator (not shown) located in an upper portion of the cabinet 102. The placement of at least a portion of the environmental control unit 160 near a support surface of the cabinet 102 allows for substantial mechanical isolation of the environmental control unit 160 from the remainder of the cabinet 102. A mechanical isolation mount is further detailed with respect to FIG. 13.

Figure 4:
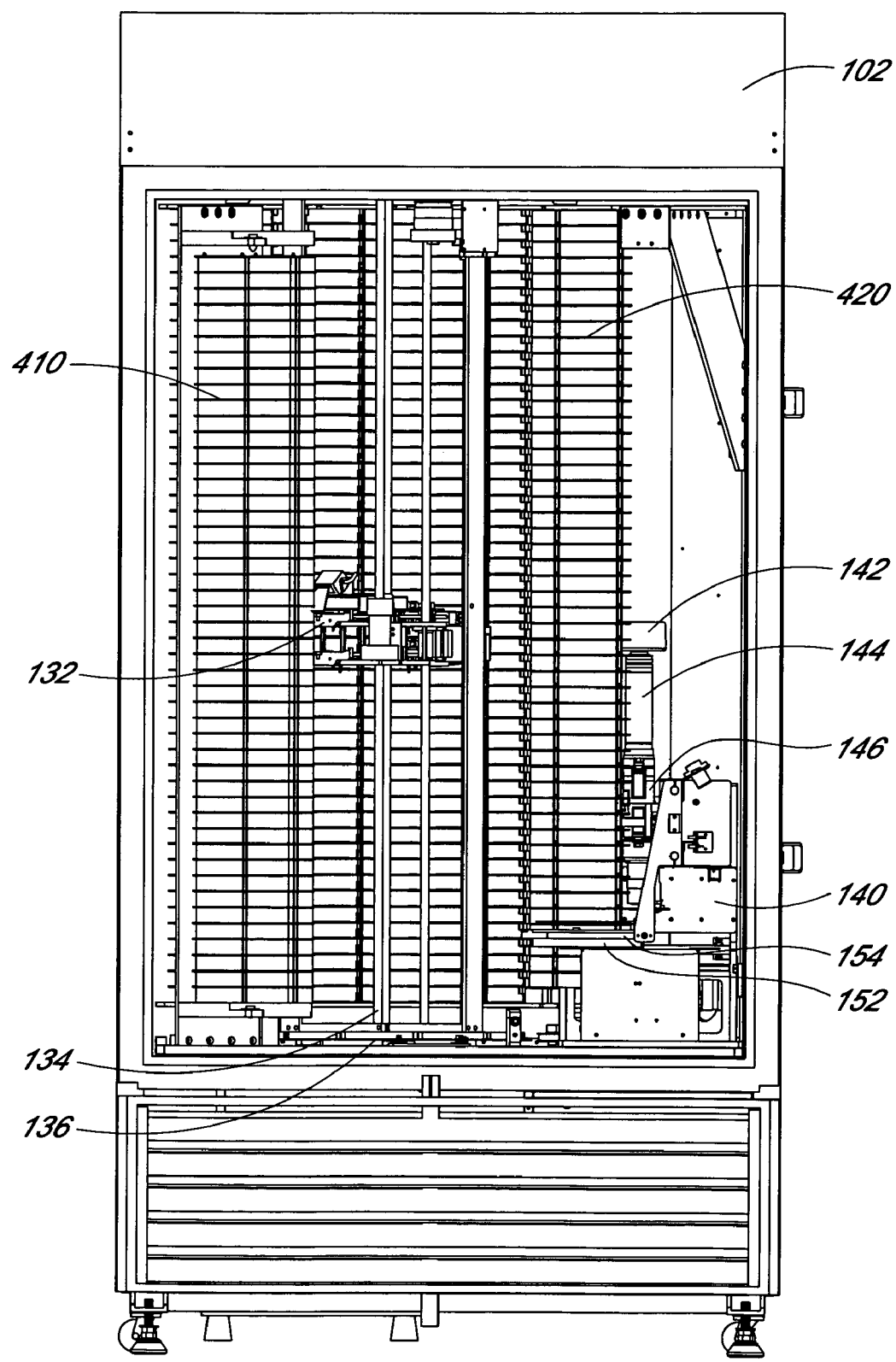
FIG. 4 is a partial view of the cabinet interior.

FIG. 4 is a partial view of the interior of the cabinet 102 with the front door 240 removed. The removable shelf system 120 and some of the shelves in the stationary shelf system 122 are not shown for the sake of clarity. The interior of the cabinet 102 can be seen through the front door opening. The interior of the cabinet 102 is the environmentally controlled chamber and all components within the interior of the cabinet 102 are within the environmentally controlled chamber.

A number of full shelf columns, for example 410, are placed in the cabinet 102 arranged at least partially around a core. Additionally, one or more partial shelf columns, for example 420, are used in locations where clearance or access is desired. The full shelf columns, 410 and partial shelf columns 420 combine to form a shelf array. All shelves within the shelf array can be configured to store sample storage receptacles, such as multi-well plates. The system can have a capacity of 330 or more multi-well plates. Alternatively, some of the shelves can be dedicated to storing items other than multi-well plates and thus are not available for sample storage. For example, a row of shelves, such as the bottom row of shelves, can be excluded from sample storage and can be used to store polarizing filters or other light filters. The polarizing filters or light filters can be used with the optical assembly 140 when imaging a sample.

The transport assembly 130 is shown in the middle of the front door opening. The transport assembly 130 is located in the core around which the shelves are arranged. The rotatable platform 136 is shown near the bottom of the front door opening. The elevator assembly 134 is mounted to the rotatable platform 136. One or more plate handlers 132 can be mounted to the elevator assembly 134. Thus, the elevator assembly is configured to raise at least one plate handler 132 up to the level of the highest shelf and can lower at least one plate handler 132 down to the level of the lowest shelf. The rotatable platform 136 is configured to rotate about a vertical axis and can position the elevator assembly 134 at any angular position along the axis of rotation. Thus, the rotatable platform 136 positions the elevator assembly 134 at the angular position of a shelf column, for example 410, and the elevator assembly positions the plate handler 132 at the height, or vertical position, of the desired shelf.

A multi-well plate retrieved by the transport assembly 130 can be transported to the optical assembly 140, shown here at the bottom right of the front door opening. The optical assembly 140 includes an illumination module 152 mounted beneath a sample mount 154. The sample mount 154 is configured to accept a multi-well plate from the transport assembly 130.

An imaging device 142, such as a CMOS camera, is connected to a lens 144 that is directed down towards the sample mount 154. The lens is connected to a movable mount 146 that is configured to position the lens 144 and imaging device 142 along a first linear axis, which can be labeled an X-axis. As described in connection with FIG. 1, the sample mount 154 can position the multi-well plate in along a second linear axis, which may be labeled a Y-axis. Thus, the optical assembly 140 is able to move a multi-well plate to any position in an X-Y plane. The movable mount 146 and sample mount 154 move to allow the imaging device 142 to capture an image of any sample well on a multi-well plate.

Figure 5:
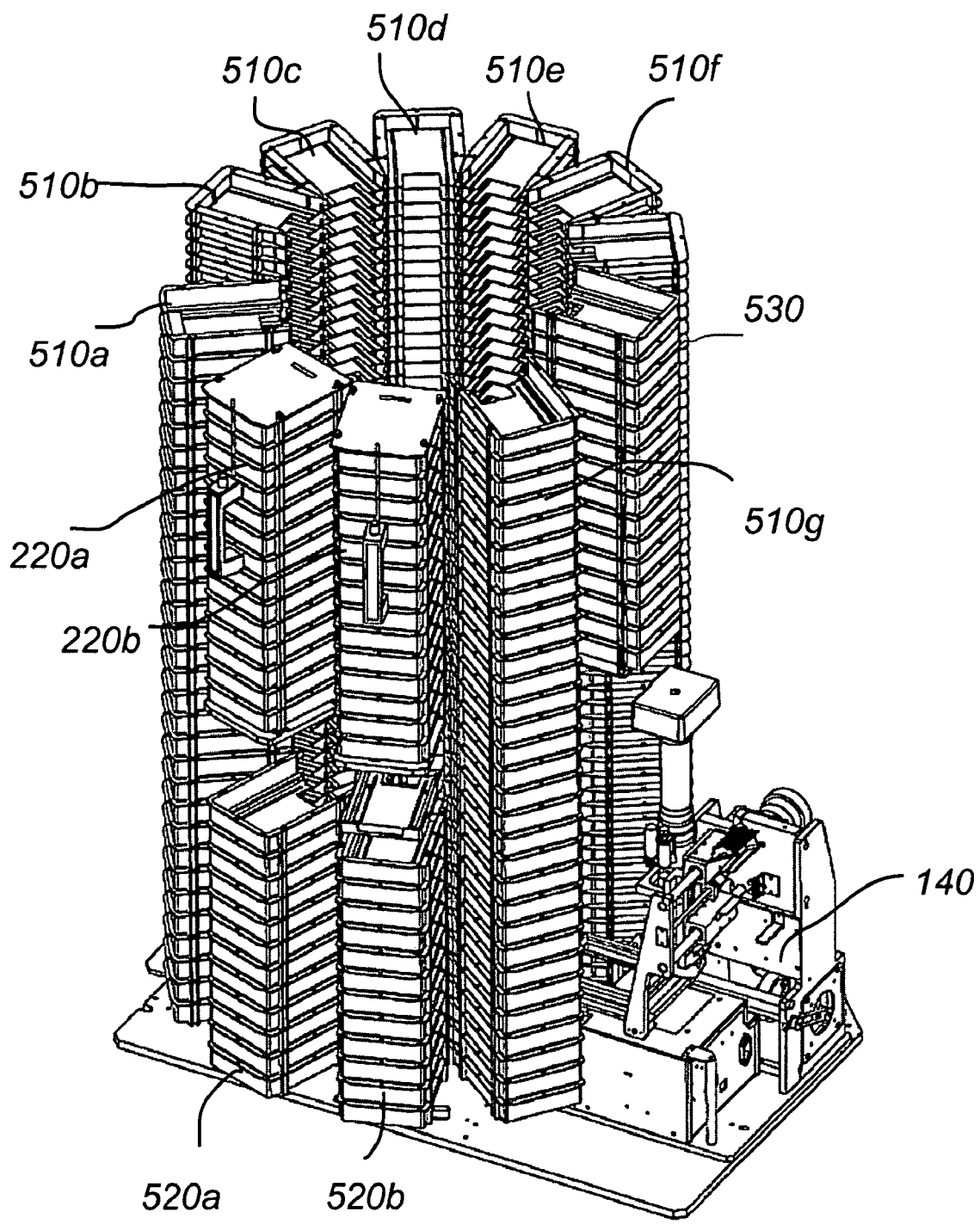
FIG. 5 is a partial view of the cabinet interior.

FIG. 5 is a partial view of portions of the system that are assembled in the interior of the cabinet 102. The cabinet 102 and transport assembly 130 are not shown for purposes of clarity. FIG. 5 clearly shows the arrangement of shelves around the core. The shelves are arranged in an arc, here substantially a circle. Within the core, or interior to the arc is located the transport assembly 130.

The shelves are arranged as a plurality of full shelf columns 510a-510g arranged in an arc around a core. A number of partial shelf columns 520a, 520b, and 530 are arranged to allow the transport assembly 130 to access the optical assembly 140 and access shelf 540, for example. The partial shelf columns 520a, 520b, and 530 allow the maximum number of shelves to be mounted within the cabinet 102.

Two of the partial shelf columns 520a and 520b are mounted beneath the removable magazines 220a and 220b. The two partial shelf columns 520a and 520b can be mounted to the front door 240, or can be mounted to the same platform on which the full shelf columns are mounted.

Another partial shelf column 530 is mounted above an access for the optical assembly 140. The transport assembly 130 thus transports multi-well plates to and from the optical assembly 140 via the access provided below the partial shelf column 530.

Figure 6:
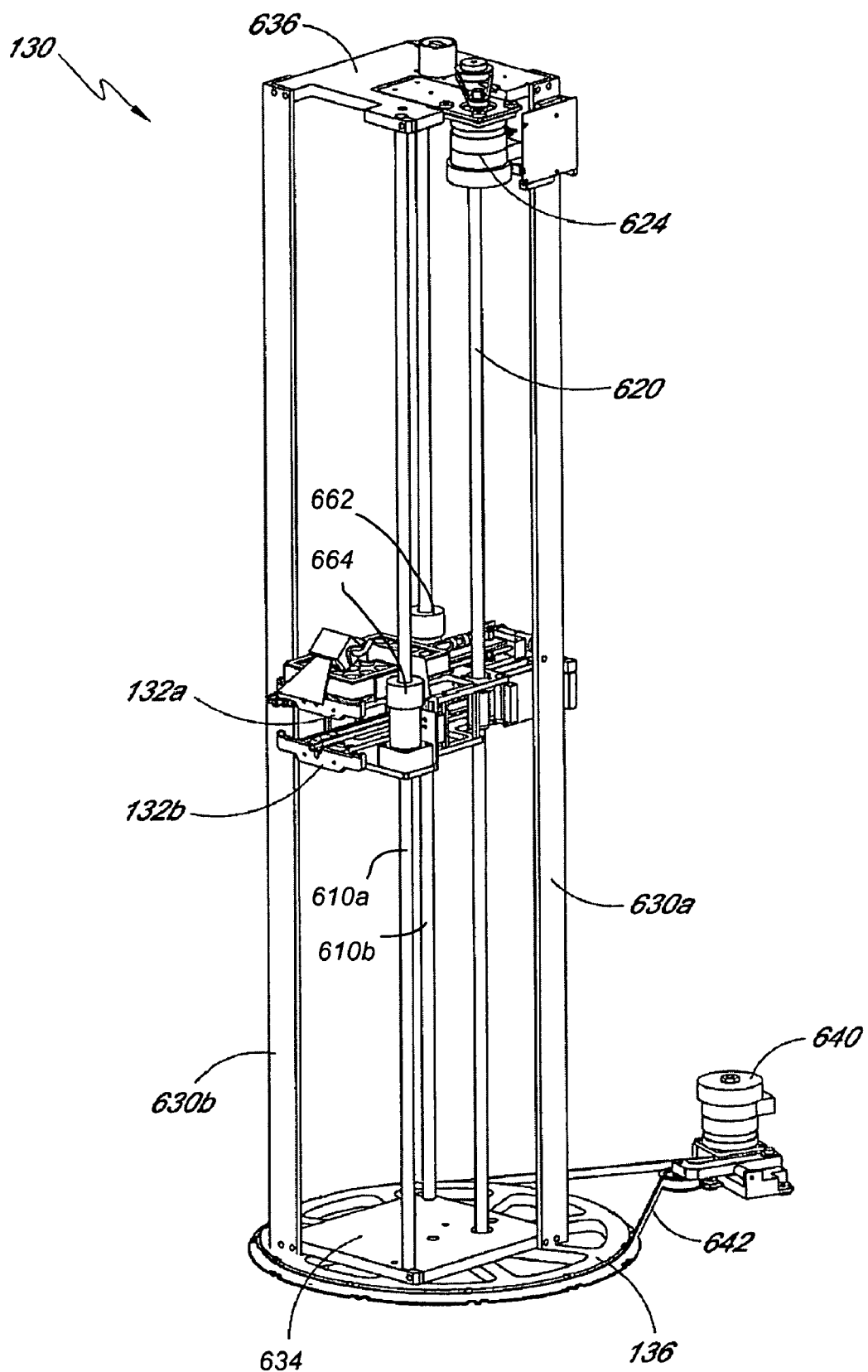
FIG. 6 is a view of the transport system.

FIG. 6 is a view of the transport assembly 130 isolated from the other components of the sample analysis system. The rotatable platform 136 is positioned using a belt 642 driven by an electric platform drive motor 640. The belt 642 can be a cogged belt and the drive wheel on the electric platform drive motor 640 can be a cogged wheel. The cogged drive wheel is typically much smaller than the rotatable platform 136 to provide increased sensitivity in angular position of the rotatable platform 136.

The rotatable platform 136 can include a receiver around the circumference of the platform to receive the cogged belt. Alternatively, the receiver can be a driven wheel attached to the rotatable platform 136. Although the drive wheel in the platform drive motor 640 is typically cogged to mate with the cogged belt 642, the receiver on the rotatable platform 136 is typically not cogged. The periodic placement of cogs on the cog belt can create vibrations when the rotatable platform 136 is rotated. This induced vibration can then be transferred to a multi-well plate or sample that is being transported by the transport assembly 130. To minimize vibrations, some, a majority, or all of the cogs can be eliminated from the receiver on the rotatable platform 136. For example, the receiver on the rotatable platform 136 can include no cogs, or a minimal number of cogs to ensure the belt 642 does not slip in the receiver.

The processor can control the platform drive motor 640 to position the rotatable platform 136 at an angular position. Alternatively, the controller 190 can position the rotatable platform at an angular position by reading position sensors that are placed on the rotatable platform 136. The processor 136 can read one or more sensors and determine the angular position of the rotatable platform 136.

Of course, the rotatable platform 136 is not limited to being driven using a belt 642. The rotatable platform 136 can also be driven using hydraulics, pneumatics, gears, chains, crank arms, friction wheels, clutches, propeller shafts, ratchets, and the like, or some other means for driving.

The elevator assembly 134 is mounted to the rotatable platform 136. The rotatable platform 136 is shown below the elevator assembly 134 but could also be mounted above or around the elevator assembly 134. The elevator assembly 134 includes a top plate 636, a base plate 634, first and second frame members 630a and 630b, first and second support rods 610a and 610b, and an acme screw 620.

The top plate 636, base plate 634 and first and second frame members 630a and 630b cooperate to form a frame to support portions of the elevator assembly 130 and plate handlers 132a and 132b. The height of the frame members 630a and 630b determine the reach of the elevator assembly 134.

The first and second support rods 610a and 610b also form part of the elevator assembly 134 frame and are also used as guides for the plate handlers 132a and 132b. A screw drive motor 624 rotates the acme screw 620 to position the height of the plate handlers 312a-b. The plate handlers 132a-b are mounted on a base that includes a threaded portion that mates with the acme screw 620. The screw drive motor 624 rotates the acme screw 620 and raises or lowers the plate handlers 132a-b depending on the direction of rotation. The controller 190 can determine a height of the plate handlers 132a-b based on a predetermined screw pitch calibration. A relatively steep screw pitch is preferred so that the elevator assembly 134 will exhibit 1, 2, 5, 10, 15, 20, or more millimeters of vertical movement per screw rotation. The large pitch keeps rotation speed low and minimizes vibration that can be transferred to the samples. Alternatively, the processor can determine the height of the plate handlers 132a-b based on sensors positioned on the plate handlers 132a-b. The elevator assembly 134 can raise and lower the plate handlers 132a-b using alternative means. For example, the elevator assembly 134 can use hydraulic pistons, pneumatic pistons, linear actuators, slides, conveyers, chain or belt drive conveyers, or other means for raising or lowering the plate handlers 132a-b.

Figure 7:
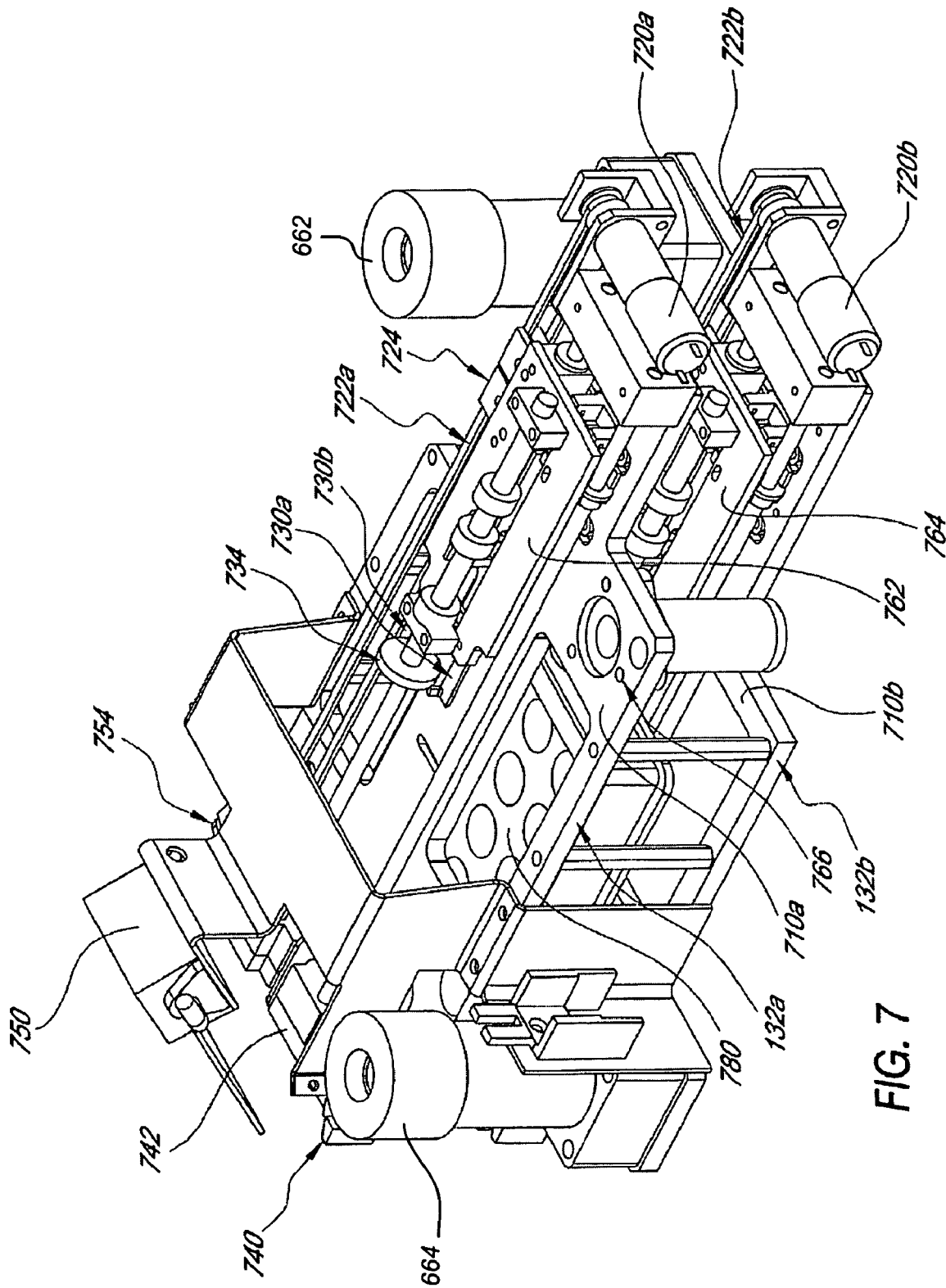
FIG. 7 is a view of the plate handler.

FIG. 7 is a view of two plate handlers 132a-b connected together. An upper plate handler 132a includes an upper base 710a, a fulcrum 740, a first slide assembly 762, a first slide motor 720a and a first slide conveyer 722a. The first slide assembly 762 includes a plate stop 734 and fingers 730a-730b. A sensor, such as an optical sensor 754, can be attached to one or more of the plate handlers 132a-b to sense a position of the plate handler 132a-b.

The first slide assembly 762 cooperates with the fulcrum 740 and elevator assembly 134 to lift and reposition a multi-well plate from a location, such as a shelf, to a position on the plate handler 132a. The fulcrum 740 can include a stepped upper surface 742 that corresponds with the various multi-well plate sizes handled by the plate handler 132a.

The lower plate handler 132b is configured similar to the upper plate handler 132a. The lower plate handler 132b includes a lower base 710b, a fulcrum (not shown), a second slide assembly 764, a second slide motor 720b and a second slide conveyer 722b. The second slide assembly 764 includes a plate stop (not shown) and fingers (not shown). The lower plate handler 132b is shown having a multi-well plate 780 positioned on the plate handler 132b. However, the multi-well plate 780 does not form a part of the plate handler 132b and is shown to illustrate the position of the multi-well plate 780 on the lower plate handler 132b.

Two support bearings 662 and 664 are mounted on the lower base 710b. The support bearings 662 and 664 ride on and align the plate handlers 132a-b with the support rods 610a-610b of the elevator assembly 134. The lower base 710b also includes a coupling mount 766 to mount the threaded coupler that interfaces with the elevator screw 620. A barcode reader 750 can be mounted to one or more of the plate handlers 132a-b to read barcodes placed on the multi-well plates.

The plate handlers 132a-b preferably do not grasp and lift the multi-well plates, but rather, gently transition the multi-well plates from the shelves to the plate handler 132a-b, thus minimizing shock and vibration experienced by the plate. A plate handler, for example 132a, lifts a first or near edge of the target plate and pulls the plate onto the plate handler 132a using the slide assembly 762.

The plate handler 132a is initially positioned at the shelf opening with the plate handler 132a below the multi-well plate so that the fingers 730a-b of the slide assembly 762 will slide underneath the near edge of the multi-well plate. The slide assembly 762 is then moved towards the multi-well plate until the stop 734 senses the slide assembly 762 is against the multi-well plate. The plate handler 132a is then raised to lift the near edge of the multi-well plate. The far edge of the multi-well plate continues to contact the shelf. As the slide assembly 762 pulls the plate onto the plate handler 132a, the fulcrum 740 contacts the bottom edge of the plate. The slide assembly 762 continues to pull the plate onto the plate handler 132a and the movement of the plate causes the fulcrum 740 to lift the second, or far, edge of the target plate. If the height of the fulcrum 740 is slightly higher than the support edge of the fingers 730a-b, the second edge of the multi-well plate will be higher than the first edge when the plate is positioned on the plate handler 132a.

The process is performed in the reverse order to place a multi-well plate from the plate handler 132a to a destination. The plate handler 132a is positioned to have the first edge of the multi-well plate slightly below the surface of the shelf and the second or far edge of the multi-well plate above the surface of the shelf. The slide assembly 762 pushes the second, or far, edge of the multi-well plate onto the shelf. The multi-well plate lifts off of the fulcrum 740 as the slide assembly 762 continues to push the multi-well plate onto the shelf until the multi-well plate is completely positioned on the shelf or other destination.

The slide assembly 762 is positioned using a slide motor 720a and slide conveyer 722a. The slide conveyer 722a can be a belt, such as a cogged belt, and the slide assembly 762 can be coupled to the slide conveyer 722a using a clamp 724. The slide motor 720a can drive the slide conveyer with a cogged wheel. The slide motor 720a can include an optical encoder to facilitate position determination. The controller 190 can determine the position of the slide assembly 762 by initially calibrating the number of encoder pulses required to move the slide assembly 762 from a first extreme to the opposite extreme. Then, the controller 190 can control the position of the slide assembly 762 by tracking the number of encoder counts. Alternatively, the controller 190 can determine the position of the slide assembly 762 using sensors connected to the slide assembly 762 or base 710a.

The inclusion of two plate handlers 132a-b in the transport assembly 130 is advantageous because a first multi-well plate can be imaged by the optical assembly 140 while the transport assembly retrieves a second multi-well plate, for example using the lower plate handler 132b. Then, after the optical assembly 140 completes the imaging of the first multi-well plate, the transport assembly 130 can position the first multi-well plate on the upper plate handler 132a and transfer the second multi-well plate to the optical assembly 140 from the lower multi-well plate 132b without moving from the optical assembly 140. The transport assembly 130 can then replace the first multi-well plate to a shelf and retrieve another multi-well plate to be imaged. Thus, the throughput of the sample imaging system is increased through the inclusion of two plate handlers 132a-b.

Additionally, the controller 190 can direct the transport assembly 130 to use the upper plate handler 132a to retrieve multi-well plates from shelves and to use the lower plate handler 132b to replace multi-well plates to shelves. Then, the processor can use the barcode reader 750 to read the barcode on the multi-well plate when it is retrieved. In this manner, the barcode on the multi-well plate can be read every time the multi-well plate is handled.

Figure 8:
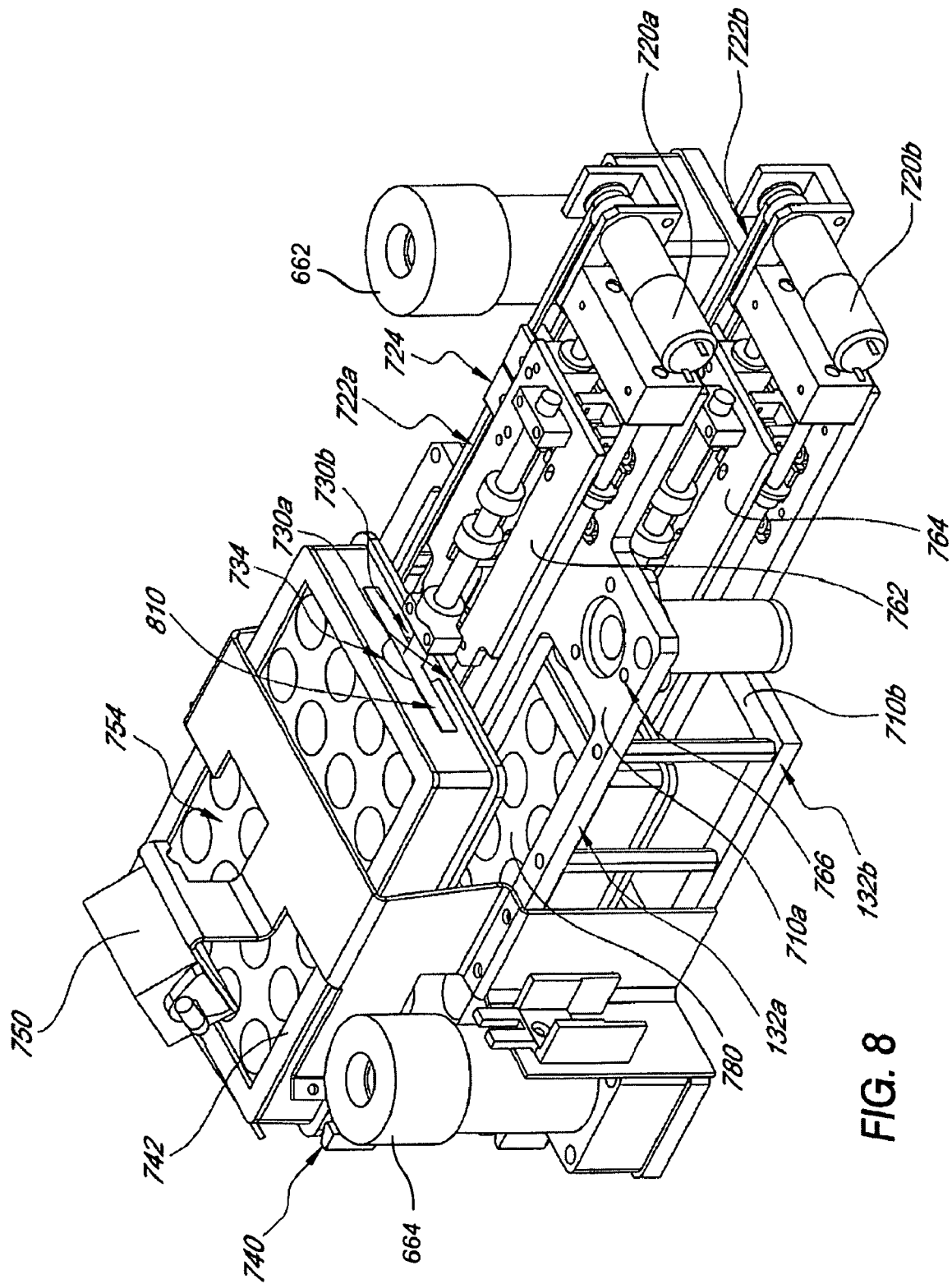
FIG. 8 is a view of the plate handler with a multi-well plate.

FIG. 8 is a duplicate of FIG. 7 except that the upper plate handler 132a is shown with a multi-well plate 802 positioned on the plate handler 132a. The barcode 810 on the multi-well plate is shown against the stop 734 of the upper plate handler 132a.

Figure 9A:
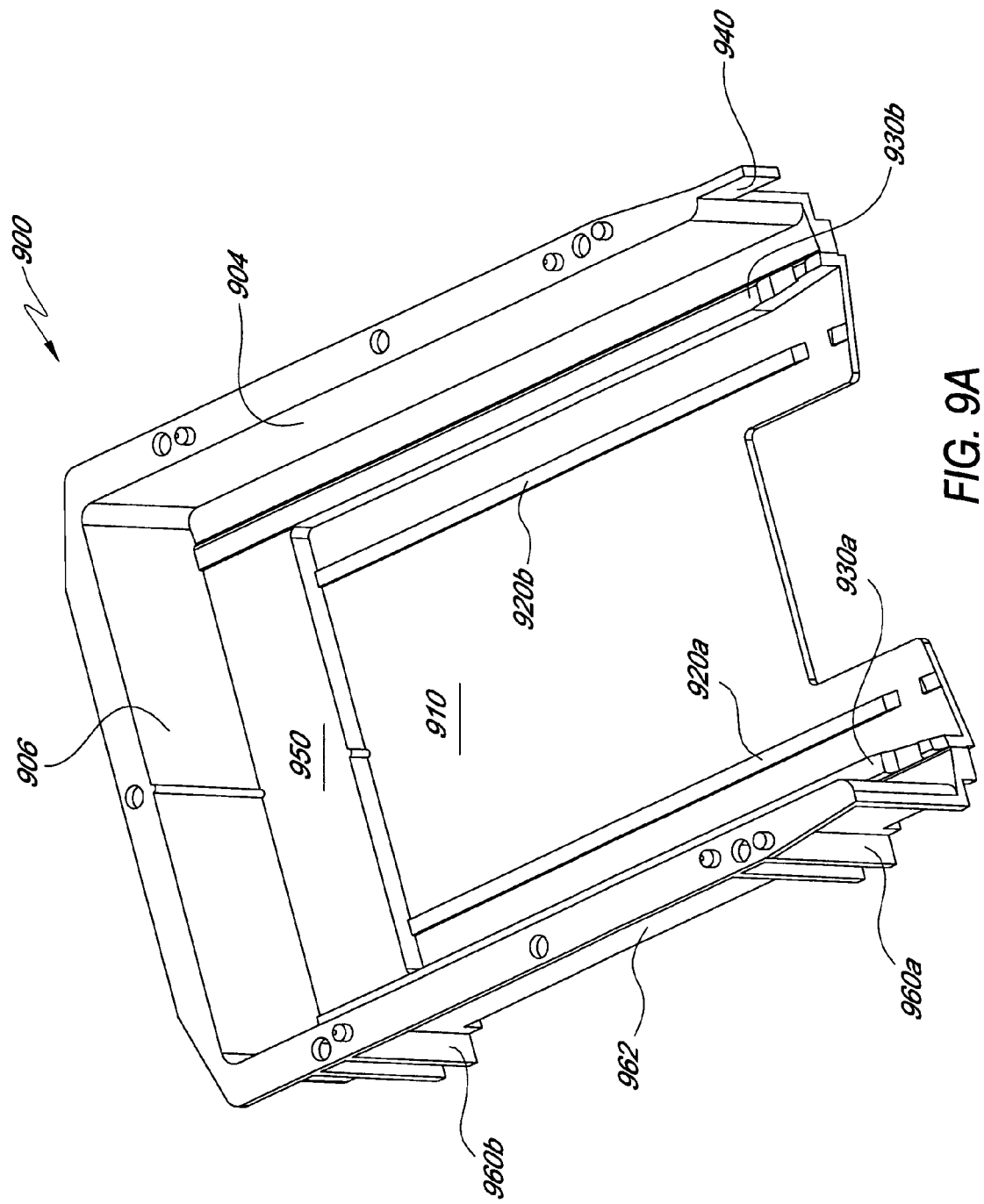
FIGS. 9A-9B are views of a shelf.
Figure 9B:
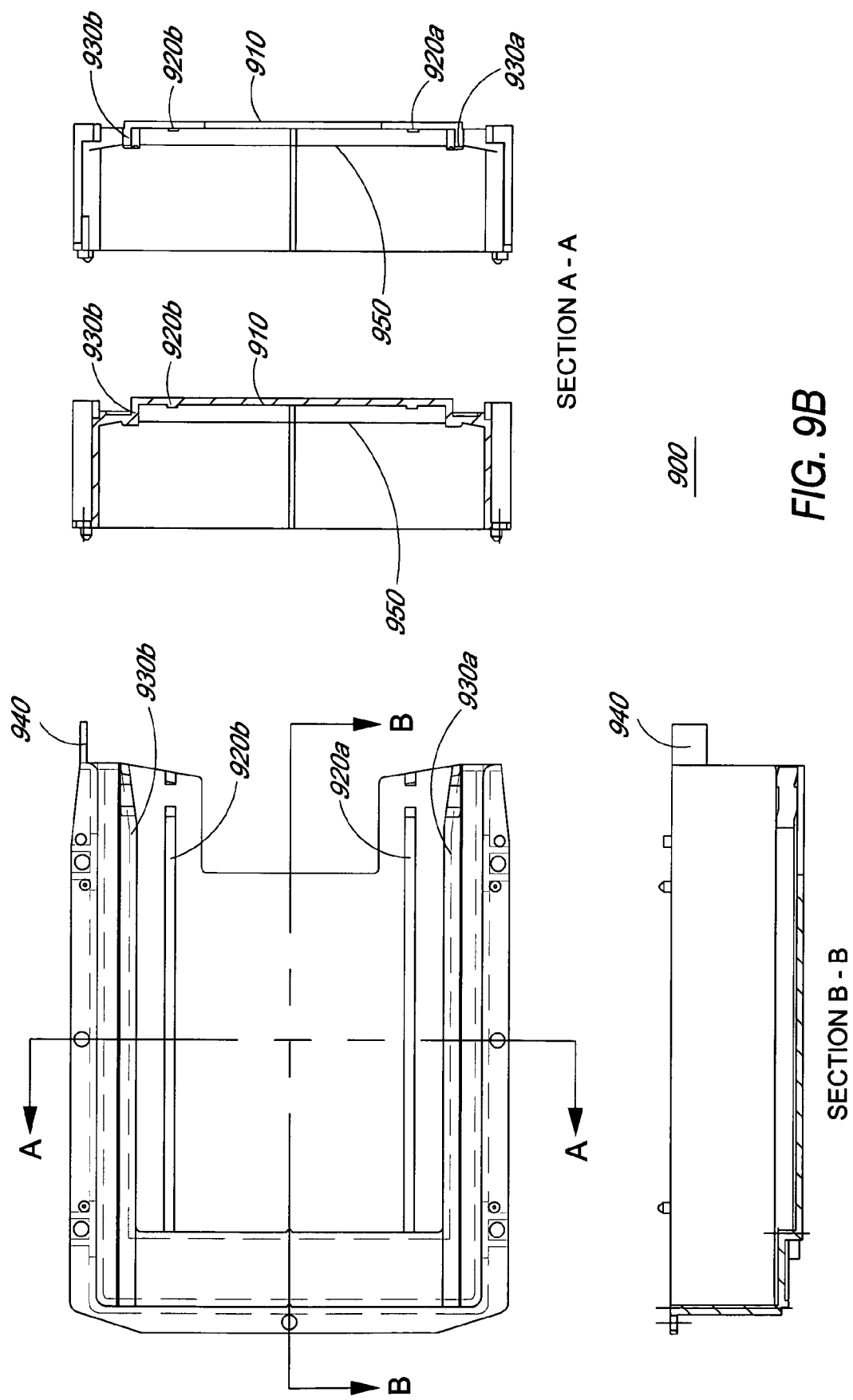

FIGS. 9A-9B are different views of a shelf 900, such as a shelf 900 that can be used in the removable shelf system 120 or the stationary shelf system 122. One or more shelves 900 can be connected to one another using hardware positioned through alignment tabs 960a and 960b integral to the sides, for example 902, of the shelf 900. Multiple shelves can be connected together to form the full shelf column 410 or the partial shelf column 420 shown in FIG. 4.

The shelf 900 includes two side walls 902, 904 and a rear wall 906. A shelf opening opposite the rear wall 906 is the shelf opening through which multi-well plates are positioned or retrieved. The shelf 900 also includes a bottom surface 910 that supports the multi-well plate when it is placed in the shelf 900. The bottom surface 910 includes a recess 912 or cutout at the front of the shelf 900 opposite the rear wall 906. The recess 912 in the bottom surface 910 allows the fingers 730a and 730b of the slide assembly 762 to be positioned beneath the front edge of a multi-well plate stored on the shelf 900.

The bottom surface 910 includes multiple rails that allow the shelf 900 to accommodate multiple multi-well plate formats. The rails can be continuous or can be interrupted. The rails are advantageously continuous to allow a multi-well plate to smoothly slide along the rail. The rails can have a single recess or step placed near the shelf 900 opening to retain a multi-well plate positioned in the shelf 900. The recess or step is advantageous when the shelf 900 is used in a removable shelf 900, such as in the removable magazine 220a shown in FIG. 2.

The largest multi-well plate format that can be accommodated by the shelf 900 rests on a first pair of rails 930a and 930b that protrude from the bottom surface 910 of the shelf 900. The first pair of rails 930a-b extend substantially the length of the shelf 900 and are substantially parallel to the shelf 900 sides 902 and 904. The first pair of rails 930a-b do not need to be parallel to the sides 902 and 904 but should extend from near the opening of the shelf 900 to the rear wall 906 of the shelf 900 in order to support a multi-well plate placed in the shelf 900. It is advantageous for the first pair of rails 930*a-b* to be substantially parallel to facilitate positioning of a smaller multi-well plate format. The side walls 902 and 904 of the shelf 900 align the largest multi-well plate accommodated by the shelf 900. Thus, the largest multi-well plate format rests on the first rails 930*a-b* and is aligned within the shelf 900 using the side walls 902 and 904.

The shelf 900 can accommodate a second smaller multi-well plate format without any changes to the shelf 900. A second pair of rails 920*a-b* is positioned in between the first pair of rails 930*a-b*. The second pair of rails 920*a-b* extend to a height that is below the height of the first pair of rails 930*a-b*. A raised stop 950 is positioned near the rear wall 906 of the shelf 900. The raised stop 950 has a height that is greater than the height of the second pair of rails 920*a-b* but is less than the height of the first pair of rails 930*a-b*. The raised stop 950 can be a ridge or wider surface. The wider surface can extend to the rear wall 906.

A smaller multi-well plate format is thus supported by the second pair of rails 920*a-b*. The first pair of rails 930*a-b* and the raised stop 950 are positioned to align the smaller multi-well plate format within the shelf 900. The second pair of rails 920*a-b* can taper towards the bottom surface 910 as the rails 920*a-b* approach the raised stop 950. The tapered rails 920*a-b* ensure the raised stop 950 provides a more positive stop for a multi-well plate.

Another advantage of the rails is to provide a smaller sliding surface on which the multi-well plates slide when they are removed and inserted. Thus, instead of sliding on the entire lower surface of the shelf 900, the multi-well plates slide primarily or solely on the rails, thus reducing vibration transferred to the multi-well plate when it is moved.

The shelf 900 can accommodate additional multi-well plate sizes by including additional rails. Alternatively, multi-well plate trays, such as the tray discussed in relation to FIG. 14, can be used to accommodate additional multi-well plate sizes. Additionally, although a pair of rails is shown for each multi-well plate size, the shelf 900 can include a single rail for each multi-well plate format and can align the multi-well plate using one side wall, for example 904, of the shelf 900. Then, rather than centering each multi-well plate format in the shelf 900, the multi-well plates are biased against one side wall 904 of the shelf 900.

The shelf 900 can also include a flag 940 or tab that the transport assembly 130 uses to determine the position of the plate handler 132 in relation to the shelf 900. The flag 740 can interrupt a light source in the optical sensor 754 on the plate handler 132. The plate handler 132 then has a known relationship to the shelf 900 when the light source from the optical sensor 754 is interrupted. The placement of the optical sensor 754 on the plate handler 132 and the placement of the flag 940 on the shelf 900 can be arranged such that the plate handler 132 is in position to retrieve or deliver a multi-well plate to the shelf 900 at the point the optical sensor 754 detects interruption of the light source.

FIG. 9B shows multiple views of the shelf 900, including a top view, a side view and two section views. The A-A section view shows the relationship of the height of the first pair of rails 930*a-b* in relation to the height of the second pair of rails 920*a-b* and the raised stop 950. The B-B section shows the placement of the flag 940 on the shelf 900.

Figure 10:
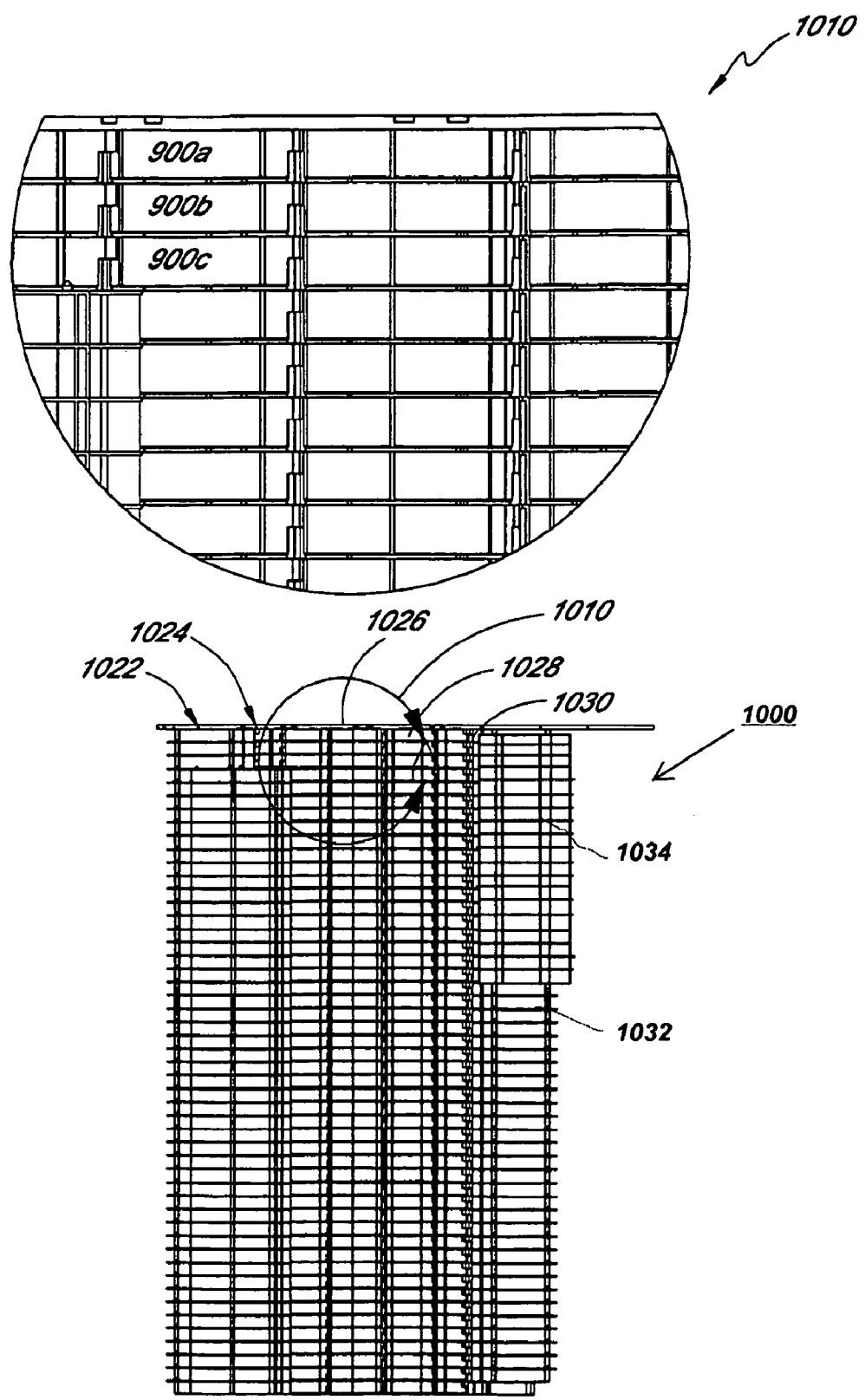
FIG. 10 is view of an array of stationary shelves.

FIG. 10 is a view of a stationary shelf array 1000 that can form a part of the stationary shelf system 122 described in FIG. 1 and shown in FIG. 5. The stationary shelf array 1000 includes multiple full shelf columns 1022, 1024, 1026, 1028, 1030, and 1032 arranged around a core. Each of the full shelf columns, for example 1022, can be the full shelf column 510*a* shown in FIG. 5. A partial shelf column 1034 is shown joined to the full shelf columns. Detail area 1010 shows the relationship of the single shelves, 900*a*-900*c* in the stationary shelf array 1000. The shelves, 900*a*-*c* are stacked vertically and are arranged along side other vertical shelf stacks.

Figure 11:
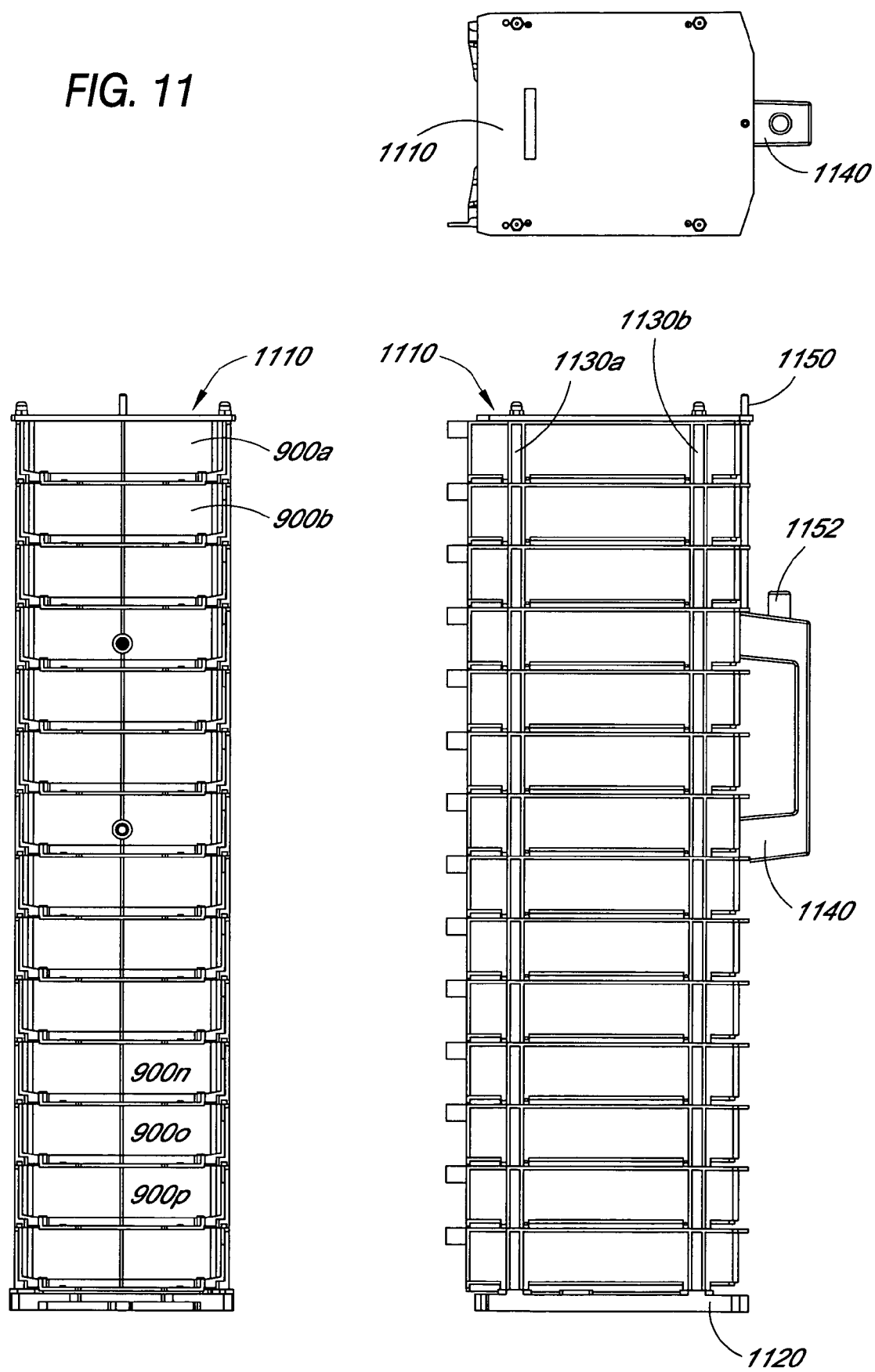
FIG. 11 is a view of a removable shelf magazine.

FIG. 11 shows three views of a removable magazine 220*a*. The front, side, and top views are shown. The removable magazine 220*a* includes a top plate 1110, a bottom plate 1120, a handle 1140, and multiple shelves 900*a*-900*p*. Sixteen shelves 900*a-p* are shown in the removable magazine 220*a*. However, the number of shelves 900*a-p* in the removable magazine 220*a* is not limited to sixteen, but can be any number.

The removable magazine 220*a* includes attachment hardware 1130*a* and 1130*b* that passes through the alignment tabs on each of the shelves 900*a-p*. The hardware 1130*a-b* can include threaded rods and nuts that clamp the top plate 1110, shelves 900*a*-, and bottom plate 1120 together to form a solid assembly.

The handle 1140 can be attached to the shelves 900*a-p* and can include a release pin 1150 or lever that is activated by a button 1152 integrated with the handle 1140. The release pin 1150 locates the removable magazine 220*a* in the cabinet 102 when the magazine 220*a* is inserted. The user can release the removable magazine 220*a* from the cabinet by depressing the button 1152 on the handle 1140.

Figure 12:
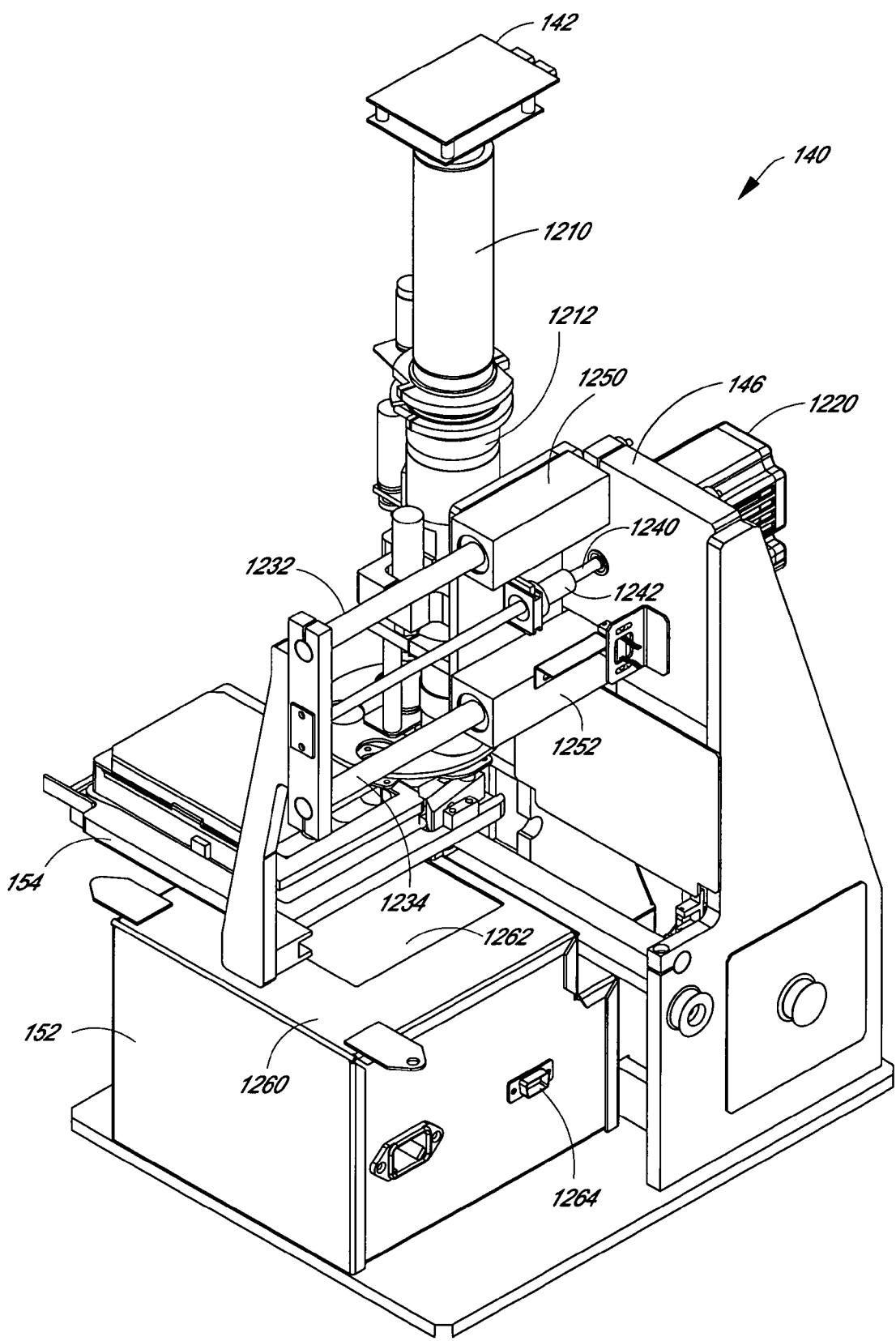
FIG. 12 is a view of the optical system.

FIG. 12 is a view of the optical assembly 140. The optical assembly 140 includes an imaging device 142 mounted to a first lens 120 and second lens 1212. The first lens 1210 and second lens 1212 combine to form the lens 144 of the optical assembly 140. Although two lenses 1210, 1212 are shown, one or more lenses can be used as the lens 144 of the optical assembly 140.

The imaging device 142 and lenses, 1210 and 1212, are connected to a movable mount 146. The movable mount 146 includes first and second support shafts 1232 and 1234 and a screw 1240 driven by a screw drive motor 1220. Bearings 1250 and 1252 are attached to, and support the imaging device 142 and lenses 1210, 1212. A drive nut 1242 attached to the imaging device 142 and lenses 1210 and 1212 is coupled to the screw 1240. The drive motor 1220 rotates the screw 1240 and the rotating motion of the screw 1240 is transferred as linear motion of the imaging device 142 and lenses 1210, 1212. The screw 1240 and support shafts 1232, 1234 are aligned to a linear axis that can be characterized as an X-axis.

The optical assembly 140 also includes a sample mount 154, here shown with a multi-well plate positioned on top of it. The sample mount 154 moves along a second linear axis substantially perpendicular to the X-axis. The second linear axis can be characterized as a Y-axis. The sample mount 154 can also be positioned using a screw drive motor and associated screw assembly (not shown).

The illumination module 152 is placed beneath the sample mount 154. The controller 190 can control the illumination module 152 to illuminate the samples in the multi-well plate. The controller 190 can control the illumination module 152 via a communication bus connector 1264. The illumination module 152 includes a housing 1260 having a window 1262. The housing 1260 encloses the illumination source, which can be, for example, xenon flash tubes. The window 1262 can be a glass window, such as a heat reflecting glass, to reduce the thermal radiation transferred to the samples. The housing 1260 provides further thermal isolation of the illumination sources to the samples. A fan can be positioned in the housing 1260 to provide further thermal control of the illumination sources. The fan can draw air in from the environmentally controlled portion of the cabinet and can exhaust heated air external to the cabinet.

Figure 13:
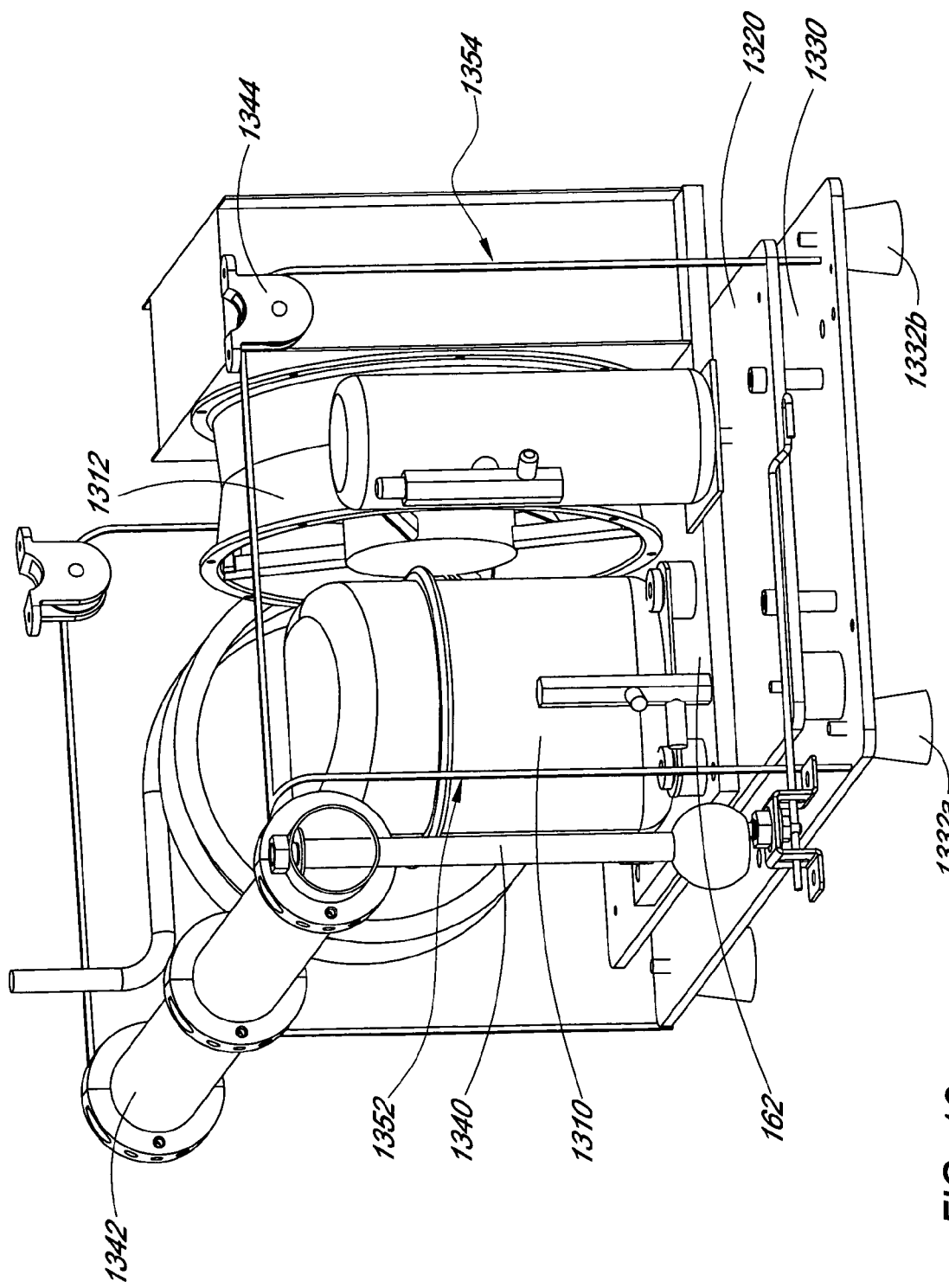
FIG. 13 is a view of the environmental control assembly.

FIG. 13 is a functional block diagram of the environmental control unit 160 and details its placement on the bottom of the cabinet 102. The environmental control unit 160 can include a refrigeration unit 162 having a compressor 1310 and fan 1312. The refrigeration unit 162 can be mounted to a support 1320 that is in turn mounted to a base plate 1330. The various mounts can be mechanical isolation mounts to reduce the amount of vibration and shock transmitted by the refrigeration unit 162 to the base plate 1330 or cabinet 102.

The base plate 1330 includes isolation mounts 1332a-b that are used to position the base plate 1330 and the associated equipment on a support surface. The support surface can be the ground on which the cabinet 102 is mounted.

The mechanical coupling between the environmental control unit 160 and the cabinet 102 is minimized by not hard mounting or supporting the environmental control unit 160 with the cabinet 102 during operation of the automated sample analysis system. However, to facilitate moving the cabinet 102 and associated environmental control unit 160, the environmental control unit 160 can be lifted off of the support surface and supported by the cabinet 102.

One embodiment of the lifting and support mechanism is illustrated in FIG. 13. The base plate 1330 is attached to first ends of a first cable 1352 and a second cable 1354. The second ends of the first cable 1352 and second cable 1354 are connected to a spool 1342. The spool 1342 is connected to a lever arm 1340. The lever arm 1340 operates to rotate the spool 1342 thereby drawing or releasing the first and second cables 1352 and 1354. The first cable 1352 is routed from the spool 1342 to a near end of the base plate 1330. The second cable 1354 is routed through a pulley 1344 to a far end of the base plate 1330. When the lever arm 1340 is moved to a first position, the first and second cables 1352 and 1354 are drawn onto the spool 1342. The action of drawing the first and second cables 1352 and 1354 onto the spool 1342 effectively shortens the cable lengths and causes the base plate to rise off of the support surface. Conversely, when the lever arm 1340 is moved to a second position, the first and second cables 1352 and 1354 are released from the spool 1342. The action of releasing the first and second cables 1352 and 1354 from the spool 1342 effectively lengthens the cable lengths and causes the base plate to lower to the support surface. The first and second cables 1352 and 1354 can be slack when the base plate 1330 rests on the support surface. Mechanical coupling between the base plate 1330 and the cabinet 102 are minimized by having the first and second cables 1352 and 1354 slack when the base plate 1330 is placed on the support surface.

The spool 1342 can be a shaft that extends the length of the cabinet 102 around which the cables can be wrapped. A similar cable configuration can then be installed on the far end of the shaft to enable the base plate 1330 to be lifted and supported by four cables. Alternatively, a duplicate lever arm, spool, and cable assembly can be positioned on the opposite side of the base plate 1330 to independently lift the opposite side of the base plate 1330.

The mechanical isolation of the base plate 1330 and environmental control unit 160 is not limited to a cable configuration. A chain lift, hydraulic lift, pneumatic lift, belts, springs, cushions, and the like, or some other means for isolation can be used to mechanically isolate the environmental control unit 160 from the cabinet 102.

Figure 14:
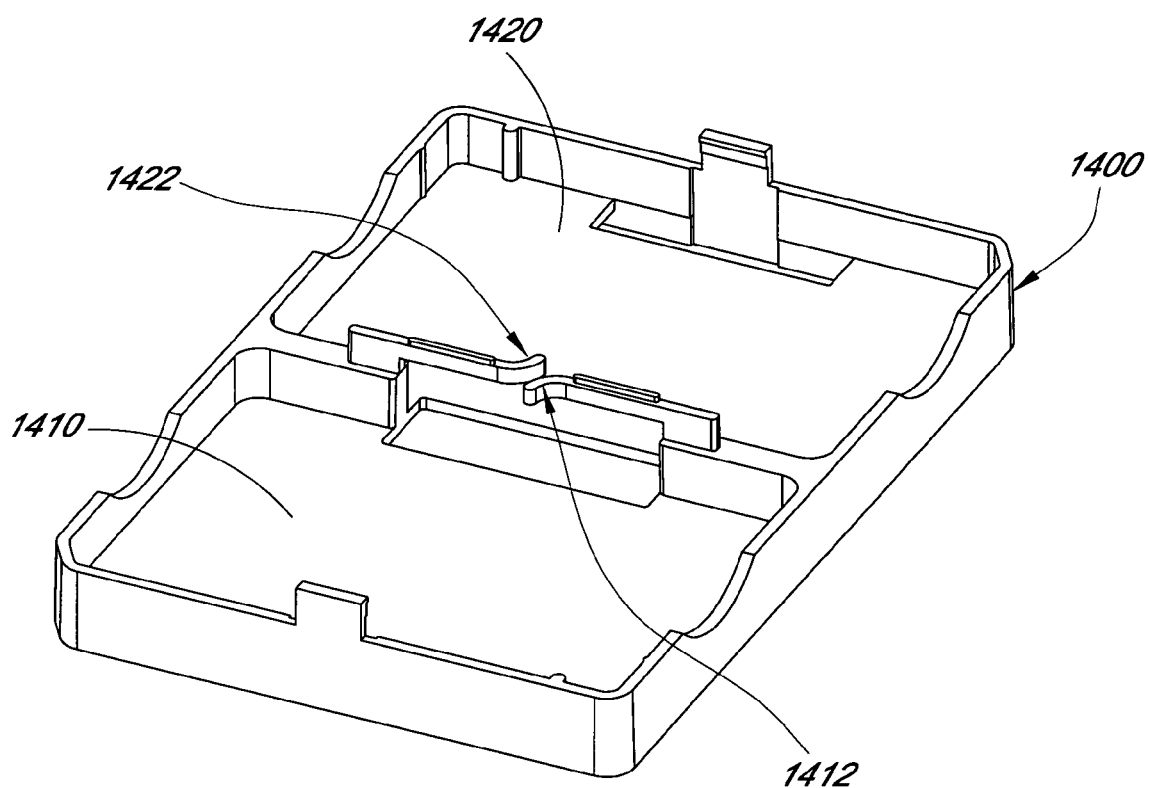
FIG. 14 is a view of a plate tray.

FIG. 14 is a view of a plate tray 1400. The plate tray 1400 substantially duplicates those areas of a multi-well plate that interface with the automated sample analysis system. For example, the plate tray 1400 has the outside dimensions about equal to a standard multi-well plate size that is supported by the automated sample analysis system. The plate tray 1400 can also include a front edge configured similar to the multi-well plate of the same outside dimension in order to interface with the fingers of the plate handlers. The plate tray 1400 can have side wall dimensions or height dimensions that mimic the dimensions of a multi-well plate for alternative plate handlers that utilize those features of the multi-well plate.

The plate tray 1400 includes recesses or cutout areas configured to hold one or more multi-well plates having at least one smaller dimension. For example, the plate tray 1400 includes two recessed areas 1410, 1420 that are configured to support smaller multi-well plates. The recessed areas 1410, 1420 can extend entirely, or partially, through the plate tray 1400. A first recessed area 1410 includes two spring fingers 1412, 1414 that locate and support the multi-well plate against an opposite wall of the recessed area 1410. The spring fingers 1412 and 1414 allow a user to insert and remove multi-well plates from the plate tray 1400 with minimal force. The spring fingers 1412, 1414 maintain sufficient force on the multi-well plate to secure it in the plate tray 1400. The second recessed area 1420 includes similar spring fingers 1422, 1424 to locate and secure a second multi-well plate in the plate tray 1400.

Figure 15:
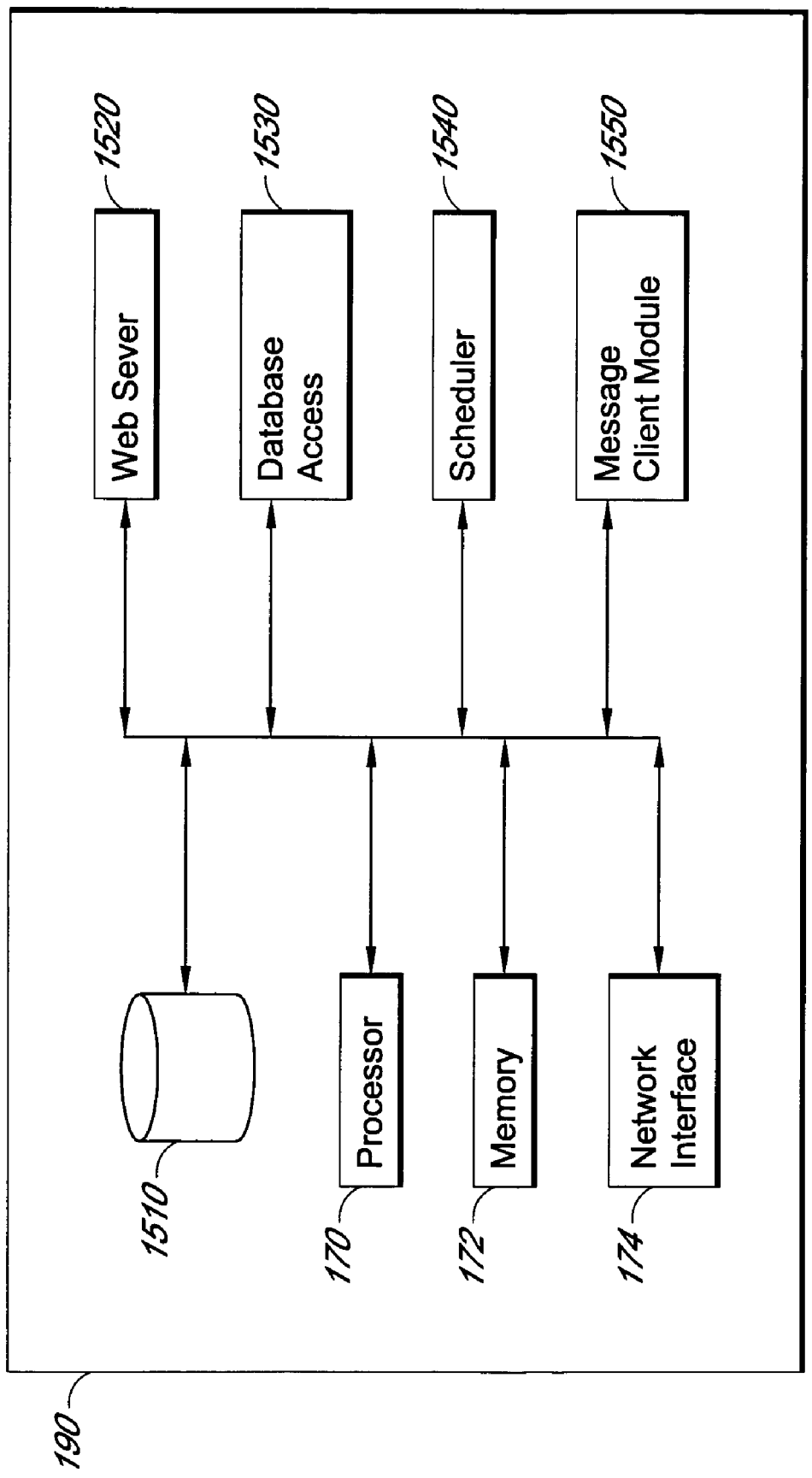
FIG. 15 is a functional block diagram of the controller.

FIG. 15 is a functional block diagram of the controller 190 of FIG. 1. The functional block diagram of FIG. 15 shows more details of the controller 190. The controller 190 includes a processor 170 in communication with a memory 172 and network interface 174 as previously described. Additionally, the controller 190 includes a database 1510, web server 1520, database access module 1530, scheduler 1540, and message client module 1550.

The web server 1520 provides another network interface. Typically, the web server 1520 interfaces with the Internet. The web server 1520 allows a user connected to the internet to access the controller 190. The web server 1520 allows a user to, for example, view sample images and modify sample scheduling using a web browser. When the network is the Internet, the user can view sample images and modify sample scheduling using a web browser in communication with the Internet from any location around the world.

The scheduler 1540 and database access module 1530 cooperate to schedule image capture of the samples stored in the shelves of the cabinet. The scheduler 1540 optimizes and schedules the plate handling tasks for all samples in the cabinet. The scheduler 1540 optimizes image capture throughput while accommodating user set priorities. The scheduler 1540 maintains a schedule of imaging tasks. The imaging task schedule can include a schedule profile that defines an imaging schedule. The imaging schedule can also include an imaging profile that defines parameters of the image capture. For example, the imaging profile can specify a particular optical filter to be used during image capture of some of the samples on a multi-well plate. The imaging schedule can also include priority levels for each sample. The priority can be predetermined by user input, or can be updated dynamically based, for example, on the degree to which a sample is overdue for image capture. Alternatively, the user priority rating and the dynamically determined priority level can be used as factors in determining a combined priority level. For example, the scheduler 1540 can weight the user priority rating and sum it with a weighted dynamically determined priority level in order to determine the combined priority level.

The scheduler 1540 also maintains a schedule of plate handling tasks. Although the majority of plate handling is performed in conjunction with imaging, the transport assembly can also handle plates for other tasks. For example, multi-well plates are moved from the magazines to the stationary shelves when the multi-well plates are first supplied to the system. Additionally, one or more plates can be moved to or from the access shelf for delivery or replacement.

The scheduler 1540 also updates the schedules upon receipt of messages from other modules. For example, the scheduler 1540 can receive new or updated schedule items from the web server 1520. Additionally, the scheduler 1540 can receive a message via the network interface 174 indicating the optical assembly is finished imaging a multi-well plate. Similarly, the scheduler 1540 can receive a message from the network interface 174 indicating the transport assembly has completed a plate movement.

The scheduler 1540 also monitors incoming messages and provides task assignments upon request by sub-systems. The scheduler 1540 can also send change messages to the sub-systems. The scheduler 1540 can manage a priority list stored in the database or other memory of all samples in the system. The priority list can also indicate a desired time for capturing images from the sample. The scheduler 1540 can use a predetermined formula or decision basis to determine the next multi-well plate that will be imaged. The scheduler 1540 can then request that the transport assembly retrieve the desired multi-well plate. The scheduler 1540 can, for example, use multi-well plate size, imaging device settings, and lens settings as factors in determining the next multi-well plate to image. Imaging throughput may be more efficient when similar sized multi-well plates are imaged in succession or if similar lens settings are used when imaging successive multi-well plates. Thus, the priority rating is not the only factor used in determining the next multi-well plate to image.

The scheduler 1540 can also maintain usage statistics. For example, the scheduler 1540 can store statistics regarding average image duration, average plate movement duration, and scheduling backlog. The scheduling backlog can, for example, include the number of hours or minutes per day scheduled over the next three months, or some other period of time.

The schedules can, for example, be stored in the database 1510. The scheduler 1540 can access the database 1510 using the database access module 1530, or can access the database 1510 independent of the database access module 1530. The database access module 1530 operates as the database interface for other modules. The database access module 1530 can operate as a single point of access to the database 1510. The database access module 1530 can then arbitrate simultaneous accesses and can prioritize database 1510 accesses, for example, based on the module requesting the access.

A message client module 1550 operates as the message interface. Internal modules direct messages to other internal modules using the message client module 1550. Additionally, external modules can send messages to the internal modules via the network interface to the message client module 1550. For example, the optical assembly or transport assembly can send messages to the scheduler 1540 using the network interface 174. The incoming messages are delivered to the message client module 1550 where they are then delivered to the scheduler 1540.

The database 1510 is used to store messages and the schedules associated with the scheduler. The database 1510 can also be used to store administrative data, such as user profiles, passwords, and system setup information. The database 1510 can be one or more storage devices and can be common with, or independent of, the memory 172.

The automated sample analysis system described above is a stand alone system that is able to operate a number of laboratory tests independent of user interaction. Once a set of multi-well plates has been loaded and scheduled for imaging, the system is able to operate without any further user intervention.

The automated sample analysis system is particularly advantageous in processes such as protein structure determination using crystallography. In such a process, samples are subject to incubation, crystallization, imaging, data collection, and crystal recognition. The automated sample analysis system can be configured to perform nearly all of these tasks independent of user supervision.

The samples can be loaded in the cabinet interior where they are incubated at a controlled environment for extensive periods of time. The controller can schedule the samples for periodic imaging. The controller can then collect the multiple images and can perform data analysis on the captured images to help perform crystal recognition. Once the crystal samples are identified by the system, a user can continue to image the crystals or can remove the crystals from the system for further analysis. Additionally, the controller can communicate image information, such as crystal recognition information, to the scheduler 1540 in order to allow the scheduler 1540 to adjust the schedule according to the crystal recognition. Further information regarding imaging of samples is included in Provisional Patent Application No. 60/474,989, titled "IMAGE ANALYSIS SYSTEM AND METHOD," filed on May 30, 2003, which is hereby incorporated by reference for all purposes.

The size of the cabinet and the arrangement of the multi-well plates in the cabinet make the automated sample analysis system particularly advantageous for use in low to middle throughput laboratory environments. The amount of floor space occupied by the system is minimal. For example, the footprint of the cabinet can be 100 cm×85 cm or less. Additionally, the systems are advantageously modular and can be combined with other systems for increased capacity or temperature variation.

For example, one or more automated sample analysis systems can be combined and operated as a single system. One of the systems can be designated a master system and the others can be designated slave systems. The systems are mechanically identical and can be controlled using a common bus connection. A master system can control the slave system over the same common bus. Thus the bus can be connected to multiple systems and each of the systems can be controlled independently over the bus.

To use the automated sample analysis system a user initially loads multi-well plates in a removable magazine. The user then inserts the removable magazine into the cabinet via the removable shelf access door. The controller can then automatically initiate a process to remove the multi-well plates from the removable magazine and place them into empty shelves in the stationary shelf system. Alternatively, the user can program the controller to initiate a process whereby the multi-well plates are removed from the removable magazine and placed in specific empty shelves within the stationary shelf system.

Regardless of the process, the controller controls the transport assembly to remove the shelves from the removable magazine. Where the transport assembly includes multiple plate handlers, as described above, more than one multi-well plate can be transported simultaneously. A first plate handler removes a first multi-well plate from the removable magazine and a second plate handler removes a second multi-well plate from the removable magazine. One or more of the plate handlers can include a barcode reader that reads a barcode affixed to the multi-well plates. The controller can then build an allocation table that relates a barcode, and thus a multi-well plate, with a shelf location. The transport assembly then transports the multi-well plates to shelves in the stationary shelf system.

The transport assembly initially locates the first plate handler at a first shelf. The controller rotates the elevator assembly, using a rotatable platform, to an angular position corresponding to a column of shelves in the stationary shelf system. The plate handler can include an optical sensor that provides an indication of the height of the plate handler relative to the shelf opening. The first plate handler then inserts the first multi-well plate into the shelf. The same process is repeated for the second plate handler having the second multi-well plate. The entire process is repeated until all of the multi-well plates are removed from the removable magazine and placed into shelves in the stationary shelf system.

The user can input an imaging schedule into the controller and can define the environmental conditions within the cabinet interior. The controller then controls the environmental control unit to produce the desired environmental conditions within the cabinet interior. The controller can also implement the imaging schedule.

To image the samples in the multi-well plates, the controller controls the transport assembly to retrieve multi-well plates from the stationary shelf system. The controller then directs the transport assembly to transport the multi-well plates to the optical assembly. The controller then controls the optical assembly to image one or more samples on the multi-well plates. The optical assembly transmits the captured images to the controller where they are stored in memory for further processing or for viewing by a user.

Initially, the controller controls the transport assembly to retrieve two multi-well plates, one for each plate handler in the transport system. The transport assembly can read the barcodes from the multi-well plates before retrieving them with the plate handlers. The transport assembly then transports the two plates to the optical assembly. The plate handler then positions the first multi-well plate into the optical assembly. The optical assembly then positions the multi-well plate for imaging by moving the multi-well plate in a first axis and moving an imaging device in a second axis. In this manner, the optical assembly can place each sample in the filed of the imaging device. The controller controls the imaging device to capture an image at the same time that the controller controls the illumination module to supply illumination to the sample. The optical assembly then transmits the captured image to the controller for storage. The controller can control the optical assembly to capture one or more images from one or more samples in the multi-well plate. Typically, the optical assembly captures at least one image of each sample in the multi-well plate. The optical assembly takes, typically, approximately 5-12 seconds to capture and transmit an image to the controller. Thus, the optical assembly takes approximately 15 minutes to capture one image of all samples in a 96 sample multi-well plate. The optical system can capture and transmit all 96 images in the 96 sample multi-well plate in as little as 4 minutes or less in some instances.

The controller then controls the plate handler to remove the first plate from the optical assembly. The controller then controls the transport assembly to position the second multi-well plate from the second plate handler onto the optical assembly. The controller then controls the optical assembly to capture images of the samples on the second multi-well plate. Concurrently, the controller controls the transport assembly to replace the first multi-well plate in its shelf. The controller then controls the transport assembly to remove the next multi-well plate scheduled for imaging. The transport assembly then transports this next multi-well plate to the optical assembly where it waits while the optical assembly completes imaging of the samples in the currently positioned multi-well plate. In this manner the transport assembly can retrieve and reposition multi-well plates while the optical assembly is imaging the samples on a different multi-well plate. Thus, it is advantageous to have at least two plate handlers in the transport assembly. Because the optical assembly takes approximately 15 minutes to image all samples in a 96 sample plate, the transport assembly does not need to quickly move the plates and, for example, can move the plates at a rate of less than 5, 2, 1, 0.8, 0.6, 0.5, 0.3, 0.2, or 0.1 cm/sec. Alternatively, the operator or user can determine a maximum acceleration that the multi-well plates are to be subjected to and adjust the system to maintain a plate acceleration below the predetermined maximum.

The system can then continue to retrieve multi-well plates and capture images of the samples according to the schedule. The system can operate indefinitely according to the schedule or can have a defined end. In this manner, the automated sample analysis system is able to efficiently and thoroughly conduct repeated sample analysis without user interaction.

Electrical connections, mechanical connections, couplings, and connections have been described with respect to various devices or elements. The connections and couplings can be direct or indirect. A connection between a first and second device can be a direct connection or can be an indirect connection. An indirect connection can include interposed elements that can process the signals from the first device to the second device.

Those of skill in the art will understand that information and signals can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

Those of skill will further appreciate that the various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the present invention.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such the processor can read information from, and write information to, the storage medium. In the alternative, the storage medium can be integral to the processor. The processor and the storage medium can reside in an ASIC.

The above description of the disclosed embodiments is provided to enable any person skilled in the art to make or use the invention. Various modifications to these embodiments will be readily apparent to those skilled in the art, and the generic principles defined herein can be applied to other embodiments without departing from the spirit or scope of the invention. Thus, the invention is not intended to be limited to the embodiments shown herein but is to be accorded the widest scope consistent with the principles and novel features disclosed herein.

What is claimed is:

1. An automated multi-well plate imaging system comprising:
   a cabinet configured to selectively provide a stabilized temperature within an interior of the cabinet;
   a plurality of stationary shelves within the interior of the cabinet, each shelf configured to store a multi-well plate, wherein the plurality of stationary shelves is arranged in a plurality of shelf columns to define an at least partially enclosed center, the plurality of shelf columns comprising full shelf columns and at least one partial shelf column, wherein the at least one partial shelf column is configured to accept a removable magazine comprising a plurality of shelves;
   a transport assembly disposed within the at least partially enclosed center so that the plurality of shelf columns at least partially surrounds the transport assembly, the transport assembly having an elevator assembly and a plate handler configured to retrieve the multi-well plate from one of the plurality of shelves, remove the multi-well plate from the shelf, and transport the multi-well plate from the shelf to a destination outside of the core; and
   an optical assembly disposed within the cabinet, outside of the at least partially enclosed center, the optical assembly having a sample mount which is the destination that receives the multi-well plate from the transport assembly, and an imaging device which images at least a portion of the multi-well plate when the multi-well plate is positioned on the sample mount.

2. The system of claim 1, further comprising a filter plate that is moved by the transport assembly to a location between the multi-well plate and an imaging device at the optical assembly.

3. The system of claim 2, wherein the filter plate comprises a polarization filter.

4. The system of claim 1, further comprising a plate adapter that is moveable by the transport assembly to the sample mount at the optical assembly, the plate adapter being configured to hold a small multi-well plate having smaller dimensions than the multi-well plate.

5. The system of claim 1, further comprising a plate tray configured to house one or more multi-well plates.

6. The system of claim 1, further comprising:
   a door attached to a front of the cabinet and configured to provide access to the interior of the cabinet; and
   a plate access door attached to the front of the cabinet and configured to provide access to a selected multi-well plate.

7. The system of claim 6, wherein the transport assembly retrieves the selected multi-well plate from one of the plurality of shelves and transports the selected multi-well plate to the plate access door.

8. The system of claim 1, further comprising a plurality of removable shelves configured to be selectively attached to the interior of the cabinet and configured to store the multi-well plate, and wherein the transport assembly is further configured to retrieve the multi-well plate from the plurality of removable shelves.

9. The system of claim 1, further comprising:
   a thermal regulation unit configured to maintain the stabilized temperature within the interior of the cabinet; and
   an isolation assembly connected to the thermal regulation unit and the cabinet and configured to substantially mechanically isolate the thermal regulation unit from the cabinet during an operating period and mechanically locate the thermal regulation unit to the cabinet during a cabinet transport period.

10. The system of claim 1, wherein the plurality of stationary shelves is arranged in an arc.

11. The system of claim 1, further comprising a second plate handler connected to the elevator assembly and configured to retrieve a second multi-well plate, wherein the elevator assembly is configured to move the first and second plate handlers at least up and down in order to retrieve multi-well plates.

12. The system of claim 1, wherein the optical assembly further comprises:
   a lens attached to a movable mount, wherein the movable mount is configured to selectively move the lens in a first direction and in a second direction perpendicular to the first direction;
   wherein the imaging device is coupled to the lens and configured to automatically capture an image of at least a portion of the multi-well plate using the lens, wherein selective movement of the lens in the first direction and the second direction allows movement of the lens so that the imaging device may capture images of substantially any portion of the multi-well plate.

13. The system of claim 12, wherein the optical assembly further comprises:
   an optical axis extending from the lens of the imaging device to an area of interest on the multi-well plate;
   a first light source positioned away from the optical axis by a first distance so that light emitted from the first light source that is incident on the area of interest on the multi-well plate is off-axis from the optical axis;
   a second light source positioned away from the optical axis by a second distance, the second light source positioned substantially opposite the optical axis from the first light source.

14. The system of claim 13, wherein the area of interest on the multi-well plate includes at least a portion of a well.

15. The system of claim 1, wherein each shelf of the plurality of shelves comprises:

a support surface having a recess to provide access to at least a portion of a bottom of a multi-well plate positioned on the shelf;

a first pair of rails secured on the support surface which directly engage and support a first multi-well plate having a first outline.

16. The system of claim 15, wherein the first pair of rails comprise outer walls on opposite sides of the support surface.

17. The system of claim 15, further comprising a second pair of rails on the support surface which directly engage and support a second multi-well plate having a second outline, the second pair of rails having a different height above the support surface from the first pair of rails.

18. The system of claim 15, further comprising first and second side surfaces having mounting guides configured to align a first shelf with a second shelf along a vertical axis.

19. The system of claim 15, further comprising:

a side surface; and a tab extending from the side surface and configured to cooperate with a sensor to provide information relating to a position relative to the support surface.

20. The system of claim 1, further comprising:

a compressor assembly associated with the cabinet and movable from a first position in which the compressor assembly is mounted to the cabinet and a second position in which the compressor assembly is seated on a floor or other support surface and is separate from and not mounted to the cabinet, whereby vibration isolation is provided between the cabinet and the compressor assembly in the second position of the compressor assembly.

21. The system of claim 1, wherein the transport assembly includes a first receptacle and a second receptacle, each receptacle adapted to receive a multi-well plate, and further comprising:

a controller linked to the transport assembly, including a computer readable medium having stored thereon one or more sequences of instructions which control the operation of the transport assembly such that while a first multi-well plate is in the sample mount, the transport assembly retrieves a second multi-well plate into the second receptacle, and then moves the first multi-well plate from the sample mount into the first receptacle and moves the second multi-well plate into the sample mount prior to returning the first multi-well plate into the storage area and retrieving a third multi-well plate.

22. The system of claim 15, wherein the first pair of rails support the first multi-well plate at a location spaced above the support surface and have upper, plate engaging sliding surfaces which slidably engage the first multi-well plate and allow sliding movement of the first multi-well plate onto and off the shelf.

23. The system of claim 1, wherein the plurality of shelf columns comprises full shelf columns and at least one partial shelf column, and wherein the at least one partial shelf column is configured to provide a passage between the at least partially enclosed area and the optical assembly disposed outside of the at least partially enclosed area.

24. The system of claim 1, further comprising a door attached to a front of the cabinet and configured to provide access to the interior of the cabinet for removal or insertion of the removable magazine.

25. An automated multi-well plate imaging system comprising:

a cabinet configured to selectively provide a stabilized temperature within an interior of the cabinet;

a plurality of stationary shelves within the interior of the cabinet, each shelf configured to store a multi-well plate, wherein the plurality of stationary shelves is arranged in a plurality of shelf columns to define an at least partially enclosed center, the plurality of shelf columns comprising full shelf columns and one or more partial shelf columns, wherein at least one partial shelf column is configured to provide a passage between the at least partially enclosed area and the optical assembly disposed outside of the at least partially enclosed area;

a transport assembly disposed within the at least partially enclosed center so that the plurality of shelf columns at least partially surrounds the transport assembly, the transport assembly having an elevator assembly and a plate handler configured to retrieve the multi-well plate from one of the plurality of shelves, remove the multi-well plate from the shelf, and transport the multi-well plate from the shelf to a destination outside of the core; and an optical assembly disposed within the cabinet, outside of the at least partially enclosed center, the optical assembly having a sample mount which is the destination that receives the multi-well plate from the transport assembly, and an imaging device which images at least a portion of the multi-well plate when the multi-well plate is positioned on the sample mount.

26. The system of claim 25, wherein the one or more partial shelf column comprises at least one second partial shelf column configured to accept a removable magazine comprising a plurality of shelves.

27. The system of claim 26, further comprising a door attached to a front of the cabinet and configured to provide access to the interior of the cabinet for removal or insertion of the removable magazine.

28. The system of claim 25, further comprising a plate adapter that is moveable by the transport assembly to the sample mount at the optical assembly, the plate adapter being configured to hold a small multi-well plate having smaller dimensions than the multi-well plate.

29. The system of claim 25, further comprising a plate tray configured to house one or more multi-well plates.

30. The system of claim 25, further comprising:

a door attached to a front of the cabinet and configured to provide access to the interior of the cabinet; and a plate access door attached to the front of the cabinet and configured to provide access to a selected multi-well plate.

31. The system of claim 30, wherein the transport assembly retrieves the selected multi-well plate from one of the plurality of shelves and transports the selected multi-well plate to the plate access door.

32. The system of claim 25, further comprising a plurality of removable shelves configured to be selectively attached to the interior of the cabinet and configured to store the multi-well plate, and wherein the transport assembly is further configured to retrieve the multi-well plate from the plurality of removable shelves.

33. The system of claim 25, further comprising:

a thermal regulation unit configured to maintain the stabilized temperature within the interior of the cabinet; and an isolation assembly connected to the thermal regulation unit and the cabinet and configured to substantially mechanically isolate the thermal regulation unit from the cabinet during an operating period and mechanically locate the thermal regulation unit to the cabinet during a cabinet transport period.

34. The system of claim 25, wherein the plurality of stationary shelves is arranged in an arc.

35. The system of claim 25, wherein the optical assembly further comprises:
a lens attached to a movable mount, wherein the movable mount is configured to selectively move the lens in a first direction and in a second direction perpendicular to the first direction;
wherein the imaging device is coupled to the lens and configured to automatically capture an image of at least a portion of the multi-well plate using the lens, wherein selective movement of the lens in the first direction and the second direction allows movement of the lens so that the imaging device may capture images of substantially any portion of the multi-well plate.

36. The system of claim 35, wherein the optical assembly further comprises:
an optical axis extending from the lens of the imaging device to an area of interest on the multi-well plate;
a first light source positioned away from the optical axis by a first distance so that light emitted from the first light source that is incident on the area of interest on the multi-well plate is off-axis from the optical axis;
a second light source positioned away from the optical axis by a second distance, the second light source positioned substantially opposite the optical axis from the first light source.

37. The system of claim 25, wherein each shelf of the plurality of shelves comprises:
a support surface having a recess to provide access to at least a portion of a bottom of a multi-well plate positioned on the shelf;
a first pair of rails secured on the support surface which directly engage and support a first multi-well plate having a first outline.

38. The system of claim 37, wherein the first pair of rails comprise outer walls on opposite sides of the support surface.

39. The system of claim 37, further comprising a second pair of rails on the support surface which directly engage and support a second multi-well plate having a second outline, the second pair of rails having a different height above the support surface from the first pair of rails.

40. The system of claim 37, further comprising first and second side surfaces having mounting guides configured to align a first shelf with a second shelf along a vertical axis.

41. The system of claim 37, further comprising:
a side surface; and
a tab extending from the side surface and configured to cooperate with a sensor to provide information relating to a position relative to the support surface.

42. The system of claim 25, further comprising:
a compressor assembly associated with the cabinet and movable from a first position in which the compressor assembly is mounted to the cabinet and a second position in which the compressor assembly is seated on a floor or other support surface and is separate from and not mounted to the cabinet, whereby vibration isolation is provided between the cabinet and the compressor assembly in the second position of the compressor assembly.

43. The system of claim 25, wherein
the transport assembly includes a first receptacle and a second receptacle, each receptacle adapted to receive a multi-well plate, and further comprising:
a controller linked to the transport assembly, including a computer readable medium having stored thereon one or more sequences of instructions which control the operation of the transport assembly such that while a first multi-well plate is in the sample mount, the transport assembly retrieves a second multi-well plate into the second receptacle, and then moves the first multi-well plate from the sample mount into the first receptacle and moves the second multi-well plate into the sample mount prior to returning the first multi-well plate into the storage area and retrieving a third multi-well plate.

* * * * *

UNITED STATES PATENT AND TRADEMARK OFFICE
CERTIFICATE OF CORRECTION

PATENT NO.         : 7,596,251 B2                                              Page 1 of 1
APPLICATION NO. : 10/769462
DATED              : September 29, 2009
INVENTOR(S)        : Affleck et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1552 days.

Signed and Sealed this

Twenty-eighth Day of September, 2010

David J. Kappos
*Director of the United States Patent and Trademark Office*